(12) United States Patent
Williams et al.

(10) Patent No.: US 7,659,070 B2
(45) Date of Patent: *Feb. 9, 2010

US007659070B2

(54) CHARGE SWITCH NUCLEOTIDES

(75) Inventors: John G. K. Williams, Lincoln, NE (US); Gregory R. Bashford, Lincoln, NE (US); Jiyan Chen, Lincoln, NE (US); Dan Draney, Lincoln, NE (US); Nara Narayanan, Greensboro, NC (US); Bambi L. Reynolds, Lincoln, NE (US); Pamela Sheaff, Omaha, NE (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/925,722

(22) Filed: Oct. 26, 2007

(65) Prior Publication Data
US 2008/0153095 A1    Jun. 26, 2008

Related U.S. Application Data

(63) Continuation of application No. 11/154,419, filed on Jun. 15, 2005, which is a continuation of application No. 09/876,374, filed on Jun. 6, 2001, now Pat. No. 6,936,702.

(60) Provisional application No. 60/286,238, filed on Apr. 24, 2001, provisional application No. 60/209,896, filed on Jun. 7, 2000.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.1; 536/23.1; 536/24.3; 536/24.33; 536/26.6

(58) Field of Classification Search .............. 435/6, 435/91.1; 536/23.1, 24.3, 24.33, 26.6
See application file for complete search history.

(56) References Cited

U.S. PATENT DOCUMENTS 3,687,808  A    8/1972   Merigan Jr. et al.

(Continued)

FOREIGN PATENT DOCUMENTS

WO    WO 98/28440    7/1998

(Continued)

OTHER PUBLICATIONS

Ishikawa et al. "Single-Molecule Detection by Laser-Induced Fluorescence Technique with a Position-Sensitive Photon-Counting Apparatus" Jpn. J. Appl. Phys., 33:1571-1576, Mar. 1994.*
Tyagi et al. Molecular Beacons: Probes that fluoresce upon Hybridization. *Nature Biotechnology*, Mar. 1996, vol. 14, p. 303-308.
Fu et al. A DNA Sequencing Strategy that Requires only Five Bases of Known Terminal Sequence for Priming. Proc. Natl. Acad. Sci. USA, Oct. 1995, vol. 92, pp. 10162-10166.

(Continued)

*Primary Examiner*—Jezia Riley
(74) *Attorney, Agent, or Firm*—Townsend and Townsend and Crew LLP

(57) ABSTRACT

The present invention provides compounds, methods and systems for sequencing nucleic acid using single molecule detection. Using labeled NPs that exhibit charge-switching behavior, single-molecule DNA sequencing in a microchannel sorting system is realized. In operation, sequencing products are detected enabling real-time sequencing as successive detectable moieties flow through a detection channel. By electrically sorting charged molecules, the cleaved product molecules are detected in isolation without interference from unincorporated NPs and without illuminating the polymerase-DNA complex.

13 Claims, 19 Drawing Sheets

U.S. PATENT DOCUMENTS

| | | | |
|---|---|---|---|
| 3,996,345 | A | 12/1976 | Ullman et al. |
| 4,351,760 | A | 9/1982 | Khanna et al. |
| 4,415,732 | A | 11/1983 | Caruthers et al. |
| 4,458,066 | A | 7/1984 | Caruthers et al. |
| 4,725,677 | A | 2/1988 | Köster et al. |
| 4,739,044 | A | 4/1988 | Stabinsky |
| 4,793,705 | A | 12/1988 | Shera |
| 4,855,225 | A | 8/1989 | Fung et al. |
| 4,863,849 | A | 9/1989 | Melamede |
| 4,962,037 | A | 10/1990 | Jett et al. |
| 4,973,679 | A | 11/1990 | Caruthers et al. |
| 4,979,824 | A | 12/1990 | Mathies et al. |
| 4,980,460 | A | 12/1990 | Molko et al. |
| 4,996,143 | A | 2/1991 | Heller et al. |
| 5,013,831 | A | 5/1991 | Stavrianopoulos |
| 5,047,519 | A | 9/1991 | Hobbs, Jr. et al. |
| 5,151,507 | A | 9/1992 | Hobbs, Jr. et al. |
| 5,231,191 | A | 7/1993 | Woo et al. |
| 5,241,060 | A | 8/1993 | Engelhardt et al. |
| 5,260,433 | A | 11/1993 | Engelhardt et al. |
| 5,332,666 | A | 7/1994 | Prober et al. |
| 5,405,747 | A | 4/1995 | Jett et al. |
| 5,449,767 | A | 9/1995 | Ward et al. |
| 5,578,443 | A | 11/1996 | Santamaria et al. |
| 5,605,662 | A | 2/1997 | Heller et al. |
| 5,608,063 | A | 3/1997 | Hobbs, Jr. et al. |
| 5,635,608 | A | 6/1997 | Haugland et al. |
| 5,637,458 | A | 6/1997 | Frankel et al. |
| 5,714,330 | A | 2/1998 | Brenner et al. |
| 5,723,591 | A | 3/1998 | Livak et al. |
| 5,776,677 | A | 7/1998 | Tsui et al. |
| 5,795,782 | A | 8/1998 | Church et al. |
| 5,800,996 | A | 9/1998 | Lee et al. |
| 5,814,524 | A | 9/1998 | Walt et al. |
| 5,846,737 | A | 12/1998 | Kang |
| 5,863,727 | A | 1/1999 | Lee et al. |
| 5,866,336 | A | 2/1999 | Nazarenko et al. |
| 5,872,243 | A | 2/1999 | Gee et al. |
| 6,012,902 | A | 1/2000 | Parce |
| 6,090,543 | A | 7/2000 | Prudent et al. |
| 6,191,266 | B1 | 2/2001 | Wang |
| 6,210,891 | B1 | 4/2001 | Nyren et al. |
| 6,232,075 | B1 | 5/2001 | Williams |
| 6,287,821 | B1 | 9/2001 | Shi et al. |
| 6,323,186 | B1 | 11/2001 | Klaubert et al. |
| 6,391,622 | B1 | 5/2002 | Knapp et al. |
| 6,399,335 | B1 | 6/2002 | Kao et al. |
| 6,409,900 | B1 | 6/2002 | Parce et al. |
| 6,869,764 | B2 | 3/2005 | Williams et al. |
| 2003/0077610 | A1 | 4/2003 | Nelson et al. |
| 2003/0096253 | A1 | 5/2003 | Nelson et al. |
| 2003/0124576 | A1 | 7/2003 | Kumar et al. |
| 2003/0162213 | A1 | 8/2003 | Fuller et al. |
| 2004/0038215 | A1 | 2/2004 | Kumar et al. |
| 2004/0048300 | A1 | 3/2004 | Sood et al. |
| 2004/0048301 | A1 | 3/2004 | Sood et al. |
| 2004/0152104 | A1 | 8/2004 | Sood et al. |
| 2004/0152119 | A1 | 8/2004 | Sood et al. |
| 2004/0224319 | A1 | 11/2004 | Sood et al. |
| 2004/0241716 | A1 | 12/2004 | Kumar et al. |
| 2006/0211010 | A1 * | 9/2006 | Korlach et al. ............ 435/6 |

FOREIGN PATENT DOCUMENTS

| | | |
|---|---|---|
| WO | WO 00/06770 | 2/2000 |
| WO | WO 00/27521 | 5/2000 |
| WO | WO 0036151 A1 * | 6/2000 |
| WO | WO 0036152 A1 * | 6/2000 |
| WO | WO 00/58507 | 10/2000 |
| WO | WO 00/70073 | 11/2000 |
| WO | WO 0067907 A2 * | 11/2000 |

OTHER PUBLICATIONS

Haugland, "Handbook of Fluorescent Probes and Research Chemicals," *Nucleic Acid Dectection*, 8:143-178 (1996).

Agrawal et al., "Site-Specific Functionalization of Oligodeoxynucleotides For Non-Radioactive Labelling," *Tetrahedron Letters*, 31:1543-1546 (1990).

Ambrose et al., "Single-Molecule Detection With Total Internal Reflection Excitation: Comparing Signal-to-Background and Total Signals in Different Geometries," *Cytometry*, 36:224-231 (1999).

Araki et al., "Allosteric Regulation of a Ribozyme Activity Through Ligand-Induced Conformational Change," *Nucleic Acids Res.*, 26:3379-3384 (1998).

Armstrong et al., "Interaction of Substrate Analogues with *Escherichia coli* DNA-Dependent RNA Polymerase," *Eur. J. Biochem.*, 70:33-38 (1976).

Asanov et al., "Regenerable Biosensor Platform: A Total Internal Reflection Fluorescence Cell with Electrochemical Control," *Anal. Chem.*, 70:1156-1163 (1998).

Bergstrom et al., "Palladium-Mediated Coupling between Organic Disulfides and Nucleic Acid Constituents," *JACS*, 111:374-375 (1989).

Bonnaffe et al., "Potential Lipophilic Nucleotide Prodrugs: Synthesis, Hydrolysis, and Antiretroviral Activity of AZT and d4T Acyl Nucleotides," *J. Org. Chem.*, 61:895-902 (1996).

Castro et al., "Single-Molecule Detection of Specific Nucleic Acid Sequences in Unamplified Genomic DNA," *Anal. Chem.*, 69:3915-3920 (1997).

Church et al., "Multiplex DNA Sequencing," *Science*, 240:185-188 (1988).

Davis et al., "Rapid DNA Sequencing Based Upon Single Molecule Detection," *GATA*, 8(1):1-7 (1991).

Eckstein et al., "Phosphate Analogs for the Study of DNA Polymerases," *Methods in Enzymology*, 262:189-217 (1995).

Edman et al., "Conformational transitions monitored for single molecules in solution," *Proc. Natl. Acad. Sci. USA*, 93:6710-6715 (1996).

Fleischmann et al., "Whole-Genome Random Sequencing and Assembly of *Haemophilus influenzae* Rd," *Science*, 269:496-511 (1995).

Garcia, "Determination of Ion Permeability by Fluorescence Quenching," *Meth. Enzymol.*, 207:501-511 (1992).

Gebeyehu et al., "Novel biotinylated nucleotide—analogs for labeling and colorimetric detection of DNA," *Nucleic Acids Research*, 15:4513-4535 (1987).

Gibson et al., "Synthesis and application of derivatizable oligonucleotides," *Nucleic Acids Research*, 15: 6455-6467(1987).

Giusti et al, "Synthesis and Characterization of 5'-Fluorescent-dye-labeled Oligonucleotides," *PCR Methods and Applications*, 2: 223-227 (1993).

Goody et al., "The Enzymatic Synthesis of Thiophosphate Analogs of Nucleotides," *Biochem. Biophys. Acta.*, 276:155-161 (1972).

Grachev et al., "ATP γ-Anilidate; A Substrate of DNA-Dependent RNA-Polymerase of *Escherichia Coli*," *FEBS Lett.*, 49:163-166 (1974).

Grachev et al., "Studies on the functional topography of *Escherichia coli* RNA polymerase," *Eur. J. Biochem.*, 163:113-121 (1987).

Griffin et al., "Specific Covalent Labeling of Recombinant Protein Molecules Inside Live Cells," *Science*, 281:269-272 (1998).

Gupta et al., "A general method for the synthesis of 3'-sulfhydryl and phosphate group containing oligonucleotides," *Nucleic Acids Research*, 19:3019-3025 (1991).

Gyllensten et al., "PCR-based HLA Class II Typing," *PCR Methods and Applications*, 1: 91-98 (1991).

Haralambidis et al., "Preparation of base-modified nucleosides suitable for non-radioactive label attachment and their incorporation into synthetic oligodeoxyribonucleotides," *Nucleic Acids Research*, 15: 4856-4876 (1987).

Hobbs, "Palladium-Catalyzed Synthesis of Alkynylamino Nucleosides. A Universal Linker for Nucleic Acids," *J. Org. Chem.*, 54: 3420-3422 (1989).

Hunkapiller et al., "Large-Scale and Automated DNA Sequence Determination," *Science*, 254: 59-67 (1991).

Hyman, "A New Method of Sequencing DNA," *Analytical Biochemistry*, 174:423-436 (1988).

Jett et al., "High-Speed DNA Sequencing: An Approach Based Upon Fluorescence Detection of Single Molecules," *J. Biomol. Struct. Dyn.*, 7:301-309 (1989).

Ju, J., et al., "Design and Synthesis of Fluorescence Energy Transfer Dye-Labeled Primers and Their Applications for DNA Sequencing and Analysis;" *Anal. Biochem.*, vol. 231, pp. 131-140 (1995).

Kadokura, M. et al., "Efficient Synthesis of -Methyl-Capped Guanosine 5'-Triphosphate as a 5'-Terminal Unique Structure of U6 RNA *via* a New Triphosphate Bond Formation Involving Activation of Methyl Phosphorimidazolidate Using $ZnCl_2$ as a Catalyst in DMF under Anhydrous Conditions," *Tetrahedron Letters*, 38:8359-8362 (1997).

Kinjo et al., "Ultrasensitive hybridization analysis using fluorescence correlation spectroscopy," *Nucleic Acids Res.*, 23:1795-1799 (1995).

Köster et al., "A strategy for rapid and efficient DNA sequencing by mass spectrometry," *Nature Biotechnology*, 14:1123-1128 (1996).

Kreimeyer et al., "Transmembrane Transport of Adenosine 5'-Triphosphate Using a Lipophilic Cholesterol Derivative," *Angew. Chem. Int. Ed.*, 37:2853-2855 (1998).

Kreimeyer et al., "Synthesis of Acylphosphates of Purine Ribonucleosides," *Tetrahedron Letters*, 37:8739-8742, 2006.

Laws et al., "Fluorescence Quenching Studies: Analysis of Nonlinear Stern—Volmer Data," *Meth. Enzymol.*, 210:448-463 (1992).

Li et al., "Design, Synthesis, and Spectroscopic Properties of Peptide-Bridged Fluorescence Energy-Transfer Cassettes," *Bioconjugate Chem.*, 10:241-245 (1999).

Luo et al., "Fluorous Mixture Synthesis: A Fluorous-Tagging Strategy for the Synthesis and Separation of Mixtures of Organic Compounds," *Science*, 291:1766-769 (2001).

Marshall, "Rules for the visible absorption spectra of halogenated Fluorescein dyes," *Histochemical J.*, 7:299-303 (1975).

Maxam et al., "A new method for sequencing DNA," *Proc. Natl. Acad. Sci. USA*, 74: 560-564 (1977).

Narasimhan et al., "p-Benzoquinone activation of metal oxide electrodes for attachment of enzymes," *Enzyme Microb. Technol.*, 7:283-286 (1985).

Nelson et al., "Bifunctional oligonucleotide probes synthesized using a novel CPG support are able to detect single base pair mutations," *Nucleic Acids Research*, 17: 7187-7194 (1989).

Nie et al., "Probing Individual Molecules with Confocal Fluorescence Microscopy," *Science* 266:1018-1021 (1994).

Nie et al., "Real-Time Detection of Single Molecules in Solution by Confocal Fluorescence Microscopy," *Anal. Chem.* 67:2849-2837 (1995).

Paris et al., "Probing DNA sequences in solution with a monomer—excimer fluorescence color change,"*Nucleic Acids Res.*, 26:3789-2393 (1998).

Ronaghi et al., "Sequencing Method Based on Real-Time Pyrophosphate," *Science*, 281:363-365 (1998).

Sanger et al., "DNA sequencing with chain-terminating inhibitors," *Proc. Natl. Acad. Sci. USA*, 74: 5463-5467 (1977).

Sato et al., "Bimane conjugates of 5-halogenouridylic acids as fluorogenic substrates for phosphodiesterase I," *J. Chem. Research (S)*, 1:390-391 (1994).

Schecker et al., "Flow-based continuous DNA sequencing via single molecule detection of enzymatically cleaved fluorescent nucleotides," *Proc. SPIE-Int. Soc. Opt. Eng.* 2386:4-12 (1995).

Schmidt et al. "Imaging of single molecule diffusion," *Proc. Natl. Acad. Sci. USA* 93, 2926-2929 (1996).

Service, "Borrowing from biology to power the petite", *Science*, 283:27 (1999).

Smagowicz et al., "Properties of $P^3$ Esters of Nucleoside Triphosphates as Substrates for RNA Polymerase from *Escherichia coli*," *Biochem.*, 20:5538-5546 (1981).

Sproat et al., "The synthesis of protected 5'-mercapto-2', 5'-dideoxyribonucleoside-3'-O-phosphoramidites; uses of 5'-mercapto-oligodeoxyribonucleotides," *Nucleic Acids Research*, 15:4837-4849 (1987).

Steitz, "A mechanism for all polymerases," *Nature*, 391:231-232 (1998).

Suto et al., "Synthesis of -phosphate-linked Nucleoside Affinity Chromatography Resins For Protein Purification, Including Ribonucleoside Triphosphate Reductase," *Nucleosides & Nucleotides*, 17(8):1453-1471 (1998).

Sverdlov et al., "Derivatives of Guanosine Triphosphate-photoreactive Substrates of *Escherichia Coli* RNA Polymerase," *Elsevier/North-Holland Biomedical Press*, 112:296-298 (1980).

Tokunaga et al., "Single molecule imaging of fluorophores and enzymatic reactions achieved by objective-type total internal reflection fluorescence microscopy," *Biochem. and Biophys. Res. Comm.*, 235:47-53 (1997).

Tyagi et al., "Multicolor molecular beacons for allele discrimination," *Nature Biotechnol.*, 16:49-53 (1998).

Velculescu et al., "Serial Analysis of Gene Expression," *Science*, 270:484-487 (1995).

Walker et al., "Synthesis and Properties of Caged Nucleotides," *Methods in Enzymology*, 172:288-301 (1989).

Wang et al., "Design and Synthesis of New Fluorogenic HIV Protease Substrates Based On Resonance Energy Transfer," *Tetrahedron Lett.*, 31:6493-6496 (1990).

Weissleder et al., "In vivo imaging of tumors with protease-activated near-infrared fluorescent probes," *Nature Biotechnol.*, 17:375-378 (1999).

Wu et al., "Synthesis and Properties of Adenosine-5'-triphosphoro-γ-1-(5-sulfonic acid)naphthyl Ethylamidate: A Fluorescent Nucleotide Substrate for DNA-Dependent RNA Polymerase from *Escherichia coli*," *Arch. Biochem. Biophys.*, 246:564-567 (1986).

Wu et al., "An allosteric synthetic DNA," *Nucleic Acids Res.*, 1512-1516 (1999).

Xu et al., "Long-Range Electrostatic Trapping of Single-Protein Molecules at a Liquid-Solid Interface," *Science*, 281:1650-1653 (1998).

Yarbrough et al., "Synthesis and properties of fluorescent nucleotide substrates for DNA-dependent RNA polymerases,"*JBC*, 254:12069-12073 (1979).

Yarbrough et al., "Stacking Interactions in Fluorescent Nucleotide Analogs Containing 1-Aminonaphthalene-5-Sulfonate at the Phosphoryl Terminus," *JBC*, 255:9907-9911 (1980).

Yarbrough et al., "Binding of Fluorescent Analogs of GRP to the Exchangeable Nucleotide Binding Site of Tubulin," *JBC*, 256:112-117 (1981).

Zuckermann et al., "Efficient methods for attachment of thiol specific probes to the 3'-ends of synthetic oligodeoxyribonucleotides," *Nucleic Acids Research*, 15: 5305-5321 (1987).

Livak et al., "Oligonucleotides with Fluorescent Dyes at Opposite Ends Provide a Quenched Probe System Useful for Detecting PCR Product and Nucleic Acid Hybridization," *PCR Methods and Applications*, Cold Spring Harbor Laboratory Press., 4:357-362 (1995).

Hunkapiller et al., "Large-Scale and Automated DNA Sequence Determination," *Science*, 254:59-67 (1991).

Griffin, et al., "Specific Covalent Labeling of Recombinant Protein Molecules Inside Live Cells," *Science*, 281:269-272 (1998).

Lyon et al., "Confinement and Detection of Single Molecules in Submicrometer Channels" *Anal. Chem.*, 69:3400-3405 (1997).

Paige, et al., "A Comparison of Through-the-Objective Total Internal Reflection Microscopy and Epifluorescence Microscopy for Single-Molecule Fluorescence Imaging" *Single Mol.* 2(3):191-201 (2001). 3.

Chou et al., "A microfabricated device for sizing and sorting DNA molecules" *Proc. Natl. Acad. Sci USA*, 96:11-13 (Jan. 1999).

Fu et al., "A microfabricated fluorescence-activated cell sorter" *Nat. Biotech.*, 17:1109-1111 (Nov. 1999).

Ha, T., "Single-Molecule Fluorescence Resonance Energy Transfer" *Methods*, 25:78-86 (2001).

Casoli et al., "Fluorescence Correlation Spectroscopy as a Tool to Investigate Single Moleucre Probe dynamics in Thin Polymer Films" *Biol. Chem.*, 382:363-369 (Mar. 2001).

* cited by examiner

| | IDEAL CONDITION: ALL BASE AND F ADDUCTS FULLY CHARGED | | | | | IN PURE WATER |
|---|---|---|---|---|---|---|
| | Charge on indicated moiety | | Net charge | | | pH 7.0 |
| NO. | NUCLEOBASE | F | NP PROBE | PPi-F | Change | Change |
| 1 | -3 | -3 | -9 | -6 | 3 | 3.25 |
| 2 | -3 | -2 | -8 | -5 | 3 | 3.25 |
| 3 | -3 | -1 | -7 | -4 | 3 | 3.25 |
| 4 | -3 | 0 | -6 | -3 | 3 | 3.25 |
| 5 | -3 | 1 | -5 | -2 | 3 | 3.25 |
| 6 | -3 | 2 | -4 | -1 | 3 | 3.25 |
| 7 | -3 | 3 | -3 | 0 | 3 | 3.25 |
| 8 | -2 | -3 | -8 | -6 | 2 | 2.26 |
| 9 | -2 | -2 | -7 | -5 | 2 | 2.26 |
| 10 | -2 | -1 | -6 | -4 | 2 | 2.26 |
| 11 | -2 | 0 | -5 | -3 | 2 | 2.26 |
| 12 | -2 | 1 | -4 | -2 | 2 | 2.26 |
| 13 | -2 | 2 | -3 | -1 | 2 | 2.26 |
| 14 | -2 | 3 | -2 | 0 | 2 | 2.26 |
| 15 | -1 | -3 | -7 | -6 | 1 | 1.26 |
| 16 | -1 | -2 | -6 | -5 | 1 | 1.26 |
| 17 | -1 | -1 | -5 | -4 | 1 | 1.26 |
| 18 | -1 | 0 | -4 | -3 | 1 | 1.26 |
| 19 | -1 | 1 | -3 | -2 | 1 | 1.26 |
| 20 | -1 | 2 | -2 | -1 | 1 | 1.26 |
| 21 | -1 | 3 | -1 | 0 | 1 | 1.26 |
| 22 | 0 | -3 | -6 | -6 | 0 | 0.26 |
| 23 | 0 | -2 | -5 | -5 | 0 | 0.26 |
| 24 | 0 | -1 | -4 | -4 | 0 | 0.26 |
| 25 | 0 | 0 | -3 | -3 | 0 | 0.26 |
| 26 | 0 | 1 | -2 | -2 | 0 | 0.26 |
| 27 | 0 | 2 | -1 | -1 | 0 | 0.26 |
| 28 | 0 | 3 | 0 | 0 | 0 | 0.26 |
| 29 | 1 | -3 | -5 | -6 | -1 | -0.74 |
| 30 | 1 | -2 | -4 | -5 | -1 | -0.74 |
| 31 | 1 | -1 | -3 | -4 | -1 | -0.74 |
| 32 | 1 | 0 | -2 | -3 | -1 | -0.74 |
| 33 | 1 | 1 | -1 | -2 | -1 | -0.74 |
| 34 | 1 | 2 | 0 | -1 | -1 | -0.74 |
| 35 | 1 | 3 | 1 | 0 | -1 | -0.74 |
| 36 | 2 | -3 | -4 | -6 | -2 | -1.74 |
| 37 | 2 | -2 | -3 | -5 | -2 | -1.74 |
| 38 | 2 | -1 | -2 | -4 | -2 | -1.74 |
| 39 | 2 | 0 | -1 | -3 | -2 | -1.74 |
| 40 | 2 | 1 | 0 | -2 | -2 | -1.74 |
| 41 | 2 | 2 | 1 | -1 | -2 | -1.74 |
| 42 | 2 | 3 | 2 | 0 | -2 | -1.74 |
| 43 | 3 | -3 | -3 | -6 | -3 | -2.74 |
| 44 | 3 | -2 | -2 | -5 | -3 | -2.74 |
| 45 | 3 | -1 | -1 | -4 | -3 | -2.74 |
| 46 | 3 | 0 | 0 | -3 | -3 | -2.74 |
| 47 | 3 | 1 | 1 | -2 | -3 | -2.74 |
| 48 | 3 | 2 | 2 | -1 | -3 | -2.74 |
| 49 | 3 | 3 | 3 | 0 | -3 | -2.74 |

*FIG. 2*

| Compound | Charge | Name | Structure |
|---|---|---|---|
| 50 | N = -2 F = +2 | DBA-U-BQS-TAMRA X | 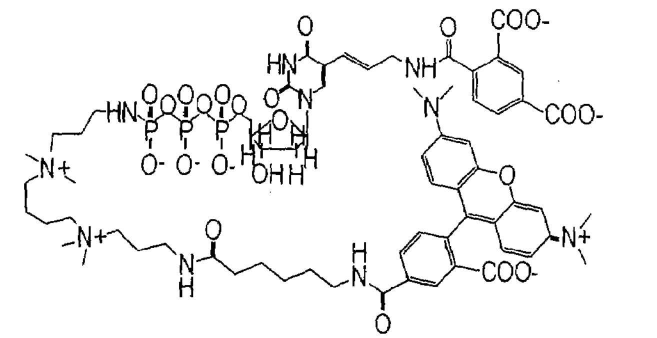 |
| 51 | N = -2 F = +1 | DBA-U-BQS-Oregon 500 | 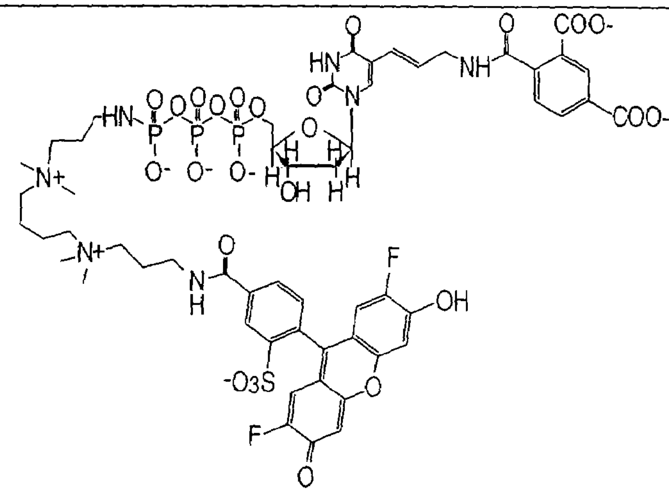 |
| 52 | N = -1 F = +2 | SUC-U-BQS-TAMRA X | 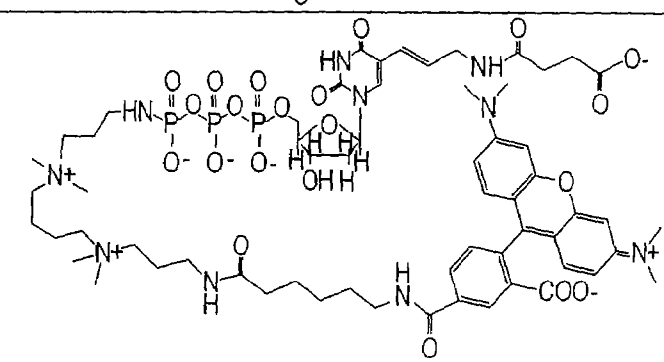 |

*FIG. 6A*

| 53 | N = +2 F = +1 | PAA-A-BQS-Oregon 500 | |
|---|---|---|---|
| 54 | N = +2 F = 0 | PAA-U-BQS-Alexa 488 | |

*FIG. 6B*

| 55 | N = -1 F = +1 | Suc-U-peptide+2-Oregon 500 | |
|---|---|---|---|
| 56 | N = 0 F = 2 | T-BQS-TAMRA X | |
| 57 | N = 0 F = 2 | T-BQS-TAMRA | |

*FIG. 6C*

| # | | | |
|---|---|---|---|
| 58 | N = +1 F = +1 | AA-U-BQS-Oregon 500 | |
| 59 | N = 0 F = +1 | G-BQS-Oregon 500 | |
| 60 | N = +2 F = +1 | PAA-C-BQS-Oregon 500 | |

*FIG. 6D*

Scheme 1 - MQS component

Scheme 2 - BQS linker

Scheme 3 - TQS linker

Scheme 4 TetQS linker

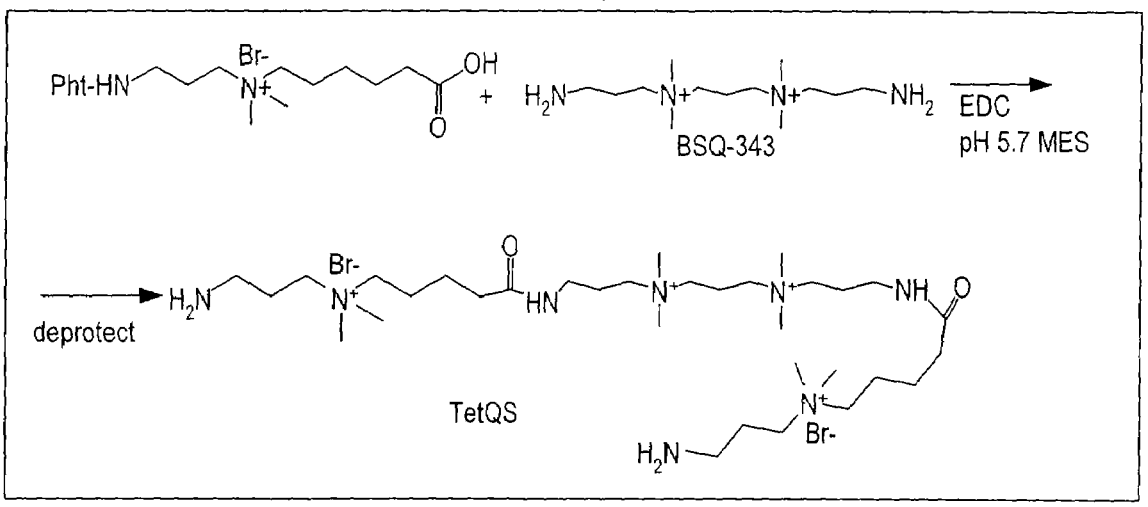

Scheme 5 - Protect AA-dUTP

Use same chemistry as in Scheme 1, except the amine is the aminoallyl group of AA-dUTP. We have shown that deprotection can be accomplished in 1M NaOH, room temp, 2 hours, without degrading triphosphates.

Scheme 6

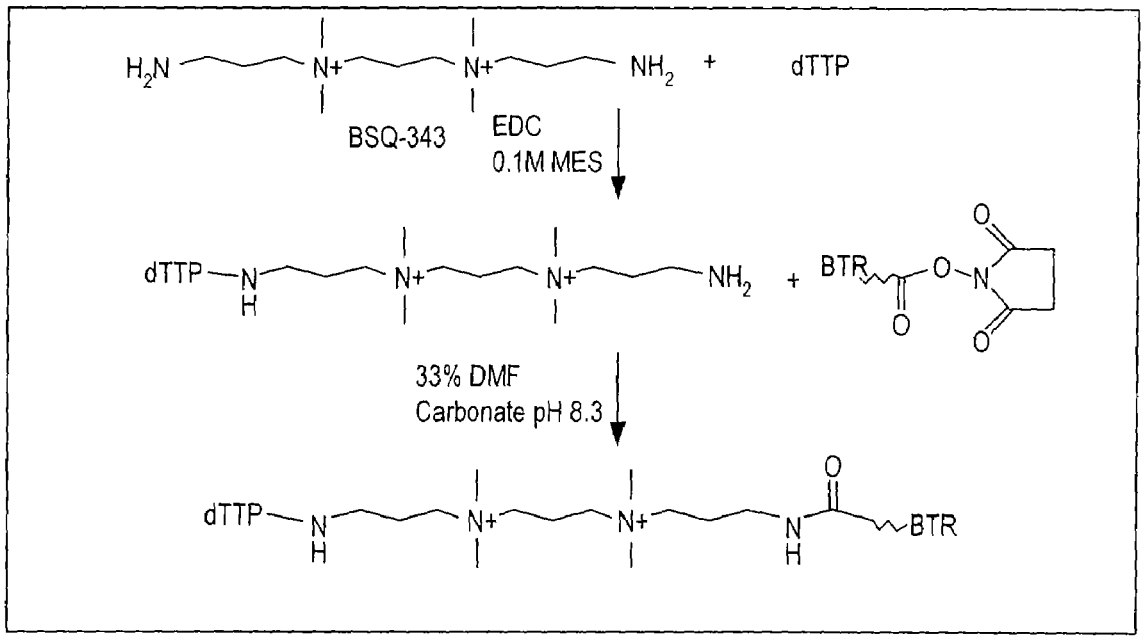

Coupling nucleotide, linker and dye (BTR is BodipyTR dye shown as the succinimide ester). We use this chemistry routinely to make γ-dNTPs (e.g, see cpd of Fig 13A)

FIG. 6E (continued)

Scheme 7 - Peptide linkers (shown in C-to-N direction)

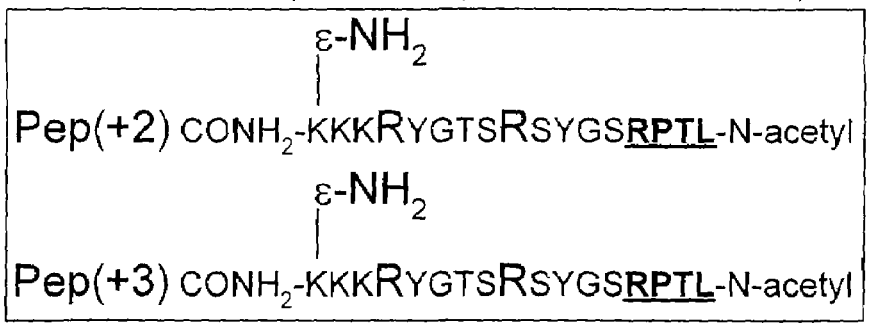

Scheme 8 - Peptide Deprotection By Thrombin Cleavage

STEP 1 couple to γ-P via ε-amine of Lysine, as in Scheme 6

STEP 2 cleave with thrombin to deprotect N-term, purify by HPLC

STEP 3 couple to dye as in Scheme 6

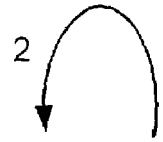

Scheme 9 - Add carboxylate to aminoally-dUTP

One Negative Charge:

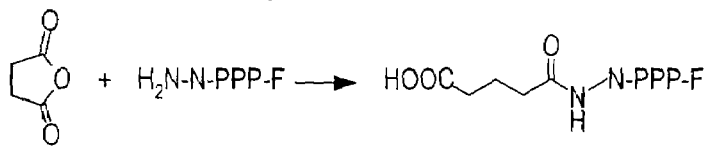

Two Negative Charges:

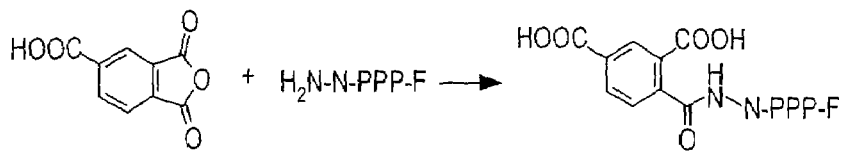

Scheme 10 - g-dNTP With Carboxylated Base

1. NH2-dU-PPP + Pht (of Scheme 1) ⟶
2. Pht-NH-dU-PPP + εNH2-KKK-pep-RPTL ⟶
3. Pht-NH-dU-PPP-KKK-pep-RPTL + 1M NaOH ⟶
4. NH2-dU-PPP-KKK-pep-RPTL + anhydride (of Sche
5. (COO⁻)-dU-PPP-KKK-pep-RPTL + thrombin ⟶
6. (COO⁻)-dU-PPP-KKK-pep-NH2 + SE-Dye ⟶
7. (COO⁻)-dU-PPP-KKK-pep-NH-Dye

*FIG. 6F*

CHARGE SWITCH NUCLEOTIDES

CROSS-REFERENCES TO RELATED APPLICATIONS

This application claims priority to U.S. Provisional Patent Application Nos. 60/209,896, filed Jun. 7, 2000, and 60/286,238, filed Apr. 24, 2001, both the disclosures of which are hereby incorporated by reference in their entirety for all purposes. This application is related to U.S. patent application Ser. No. 11/925,724, filed on even date herewith, which is hereby incorporated by reference in its entirety for all purposes.

BACKGROUND OF THE INVENTION

The primary sequences of nucleic acids are crucial for understanding the function and control of genes and for applying many of the basic techniques of molecular biology. In fact, rapid DNA sequencing has taken on a more central role after the goal to elucidate the entire human genome has been achieved. DNA sequencing is an important tool in genomic analysis as well as other applications, such as genetic identification, forensic analysis, genetic counseling, medical diagnostics, and the like. With respect to the area of medical diagnostic sequencing, disorders, susceptibilities to disorders, and prognoses of disease conditions, can be correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations and ras proto-oncogene mutations (see, Gyllensten et al., PCR Methods and Applications, 1: 91-98 (1991); U.S. Pat. No. 5,578,443, issued to Santamaria et al.; and U.S. Pat. No. 5,776,677, issued to Tsui et al.).

Various approaches to DNA sequencing exist. The dideoxy chain termination method serves as the basis for all currently available automated DNA sequencing machines. (see, Sanger et al., *Proc. Natl. Acad. Sci.*, 74: 5463-5467 (1977); Church et al., *Science*, 240: 185-188 (1988); and Hunkapiller et al., *Science*, 254: 59-67 (1991)). Other methods include the chemical degradation method, (see, Maxam et al., *Proc. Natl. Acad. Sci.*, 74: 560-564 (1977), whole-genome approaches (see, Fleischmann et al., *Science*, 269, 496 (1995)), expressed sequence tag sequencing (see, Velculescu et al., *Science*, 270, (1995)), array methods based on sequencing by hybridization (see, Koster et al., *Nature Biotechnology*, 14, 1123 (1996)), and single molecule sequencing (SMS) (see, Jett et al., *J. Biomol. Struct. Dyn.* 7, 301 (1989) and Schecker et al., *Proc. SPIE-Int. Soc. Opt. Eng.* 2386, 4 (1995)).

PCT Application No. US99/29585, filed Dec. 13, 1999, and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader. Electro-osmotic flow requires a fixed charge on the solid support and a voltage gradient (current) passing between two electrodes placed at opposing ends of the solid support. The flow chamber can be divided into multiple channels for separate sequencing.

Much more recently, PCT Application No. US00/13677, filed May 18, 2000, discloses a method of sequencing a target nucleic acid molecule having a plurality of bases. The temporal order of base additions during the polymerization reaction is measured on a molecule of nucleic acid. The activity of a nucleic acid polymerizing enzyme on the template nucleic acid molecule is thereafter followed in time. The sequence is deduced by identifying which base is being incorporated into the growing complementary strand of the target nucleic acid by the polymerizing enzyme at each step in the sequence of base additions. The steps of providing labeled nucleotide analogs, polymerizing the growing nucleic acid strand, and identifying the added nucleotide analog are repeated so that the nucleic acid strand is further extended and then sequenced.

In addition, U.S. Pat. No. 4,979,824, describes that single molecule detection can be achieved using flow cytometry wherein flowing samples are passed through a focused laser with a spatial filter used to define a small volume. Moreover, U.S. Pat. No. 4,793,705 describes a detection system for identifying individual molecules in a flow train of the particles in a flowcell. The patent further describes methods of arranging a plurality of lasers, filters and detectors for detecting different fluorescent nucleic acid base-specific labels.

Single molecule detection on solid supports is described in Ishikawa, et al. *Jan. J. Apple. Phys.* 33:1571-1576. (1994). As described therein, single-molecule detection is accomplished by a laser-induced fluorescence technique with a position-sensitive photon-counting apparatus involving a photon-counting camera system attached to a fluorescence microscope. Laser-induced fluorescence detection of a single molecule in a capillary for detecting single molecules in a quartz capillary tube has also been described. The selection of lasers is dependent on the label and the quality of light required. Diode, helium neon, argon ion, argon-krypton mixed ion, and Nd:YAG lasers are useful in this invention (see, Lee et al. (1994) *Anal. Chem.*, 66:4142-4149).

A need currently exists for more effective and efficient compounds, methods, and systems for single molecule detection, especially as they relate to single molecule DNA sequencing. These and further needs are provided by the present invention.

BRIEF SUMMARY OF THE INVENTION

The present invention relates to compounds, methods and systems to determine and elucidate sequences of nucleic acids. Advantageously, the compounds, methods and systems of the present invention can be used to sequence nucleic acid rapidly and without the need for amplification or cloning.

In one embodiment, the present invention provides a charge-switch nucleotide phosphate (NP) probe, comprising: an intact NP probe having a terminal phosphate with a fluorophore moiety attached thereto, the intact NP probe having a first molecular charge associated therewith, whereupon cleavage of the terminal phosphate as a phosphate fluorophore moiety, the phosphate fluorophore moiety carries a second molecular charge, wherein the difference between the first molecular charge and the second molecular charge is at least 0.5. Preferably, the difference between the first molecular charge and the second molecular charge is at least 0.5 as calculated in pure water at pH 7.0. In preferred aspects, the charge difference is between about 1 and about 4, and any fraction therebetween. In certain preferred embodiments, the NP probe has a positive charge, or alternatively, upon cleavage of the terminal phosphate as a phosphate fluorophore moiety, the phosphate fluorophore moiety carries a positive charge relative to the NP probe.

In a preferred aspect, the NP probe is a nucleotide triphosphate (NTP), and the terminal phosphate is a γ-phosphate with a fluorophore moiety attached thereto. In certain aspects, the NP probe is incorporated into a growing nucleic acid strand that is complementary to a target nucleic acid, where upon a γ-phosphate with a fluorophore moiety attached thereto is released as a detectable pyrophosphate moiety.

In one embodiment, the present invention provides an intact charge-switch nucleotide phosphate (NP) probe, wherein, upon enzymatic cleavage of the intact charge-switch NP probe to produce a phosphate detectable moiety, the phosphate detectable moiety migrates to an electrode, and the intact charge-switch NP probe migrates to the other electrode.

In another embodiment, the present invention provides a method for separating a labeled nucleotide phosphate having a detectable moiety from a released charged detectable moiety in a sample stream, the method comprising: a) immobilizing a complex comprising a nucleic acid polymerase or a target nucleic acid onto a solid support in a single molecule configuration; b) contacting the complex with a sample stream comprising a target nucleic acid when the polymerase is immobilized, or a polymerase when the target nucleic acid is immobilized, a primer nucleic acid which complements a region of the target nucleic acid; and a labeled nucleotide phosphate having a detectable moiety, wherein the detectable moiety is released as a charged detectable moiety when the NP is incorporated into the primer nucleic acid; and c) applying an energy field to the sample stream, thereby separating the labeled NP from the charged detectable moiety.

In certain aspects, the NP is a labeled nucleotide triphosphate (NTP) having a detectable moiety and the detectable moiety is a γ-phosphate with a fluorophore moiety attached thereto. In a preferred aspect, the charge of the detectable moiety after release is different than the labeled nucleotide phosphate (NP) having a detectable moiety attached thereto.

In another embodiment, the present invention provides a method for sequencing a target nucleic acid comprising: a) immobilizing a complex comprising a nucleic acid polymerase, or a target nucleic acid onto a solid support in a single molecule configuration; b) contacting the complex with a sample stream comprising a target nucleic acid when the polymerase is immobilized, or a polymerase when the target nucleic acid is immobilized, a primer nucleic acid which complements a region of the target nucleic acid of the region to be sequenced; and a labeled nucleotide phosphate (NP) having a detectable moiety, wherein the detectable moiety is released as a charged detectable moiety when the NP is incorporated into the primer nucleic acid wherein the solid support is disposed in a flowcell having an inlet port and an outlet port; c) applying an energy field to the sample stream; and d) detecting the charged detectable moiety, thereby sequencing the target nucleic acid. In preferred aspects, the energy field is a first energy field such as an electric field applied in the transverse direction, and a second energy filed such as a pressure field applied in the axial direction. The nucleotide phosphate is preferably a nucleotide triphosphate.

Suitable nucleobases include, but are not limited to, adenine, guanine, cytosine, uracil, thymine, deazaadenine and deazaguanosine. In a preferred embodiment, the NPs are charge-switch γ-phosphate labeled dNTP. In one aspect, the polymerase is immobilized and the sample stream contains a target nucleic acid. In another aspects, the target nucleic acid is immobilized and the sample stream contains polymerase. In another aspect, the method includes applying an electric field transverse to the sample stream to sort between a reagent and a product.

In yet another aspect, the present invention provides a system that can be used to facilitate the contact of fluorescent-labeled nucleotides with polymerases, and thereafter remove them away (while emitting signals) from the optical field of view. The system is especially beneficial in single-molecule sequencing schemes to facilitate detection. As such, the present invention provides a microfabricated flowcell system for single-molecule detection, comprising: a) a flowcell having an inlet port and an outlet port wherein a sample stream having a detectable analyte flows therethrough; b) an energy field source applied to the sample stream; and c) a detector for detecting the analyte.

In certain aspects, the system comprises two energy fields, one axial to the sample stream and the other energy field applied in the transverse direction. Preferably, the applied fields are electric fields, pressure fields and combinations thereof. The fields are variable, thus permitting control of the motion of the nucleotides and (after incorporation) the phosphate detectable moiety (e.g., fluorescent-labeled phosphate).

In certain embodiments, the flowcell has multiple inlet ports and multiple outlet ports wherein a sample stream having detectable analytes flow therethrough. In addition to a first energy field and a second energy field, in certain aspects, the flowcell of the present invention comprises an array of energy fields disposed throughout the flowcell arrangement and an array of immobilized polymerases, target nucleic acids and combinations thereof in single molecule configuration. This arrangement can be used to analyze a plurality of nucleic acids in a single flowcell device.

Numerous benefits and advantages are achieved by way of the present invention over conventional compounds, methods and systems. For example, the charge-switch nucleotide phosphates allow separation of the cleaved terminal phosphate (e.g., pyrophosphate) from the intact nucleotide phosphate probe reagents. This characteristic is useful for single-molecule DNA sequencing in a microchannel sorting system with an energy field. Using 4 different NTPs each labeled with a unique dye, real-time DNA sequencing is possible by detecting the released pyrophosphate having different labels. By electrically sorting differently-charged molecules in this manner, the cleaved PPi-Dye molecules are detected in isolation without interference from unincorporated NTPs and without illuminating the polymerase-DNA complex.

With respect to the flowcell, the energy fields can be varied in accordance with the charge on a molecule to increase the probability of signal detection. Moreover, the flowcell of the present system increases the signal-to-noise ratio (S/N) of the detectable moiety. By increasing the S/N, a lower detection limit is possible.

These and other objects and advantages will become more apparent when read with the accompanying detailed description and drawings that follow.

BRIEF DESCRIPTION OF THE DRAWINGS

FIG. 2 tabulates various charges of charge-switch nucleotides according to the present invention. In the ideal condition, the charged groups attached to the nucleobase, sugar or on the label "F" are assumed to be in fully charged form. In the pure water condition, the effect of hydrogen ions on the net charge of the phosphate groups is calculated using equilibrium constants given by Frey and Stuhr (1972), *Journal of American Chemical Society*, 94:8818. Hydrogen ions confer a time-averaged partial positive charge preferentially to the PPi-F group as compared to the NP Probe due to the presence of the secondary ionization phosphate oxygen present only on the PPi-F group;

DETAILED DESCRIPTION OF THE INVENTION AND PREFERRED EMBODIMENTS

I. Definitions

Figure 1:
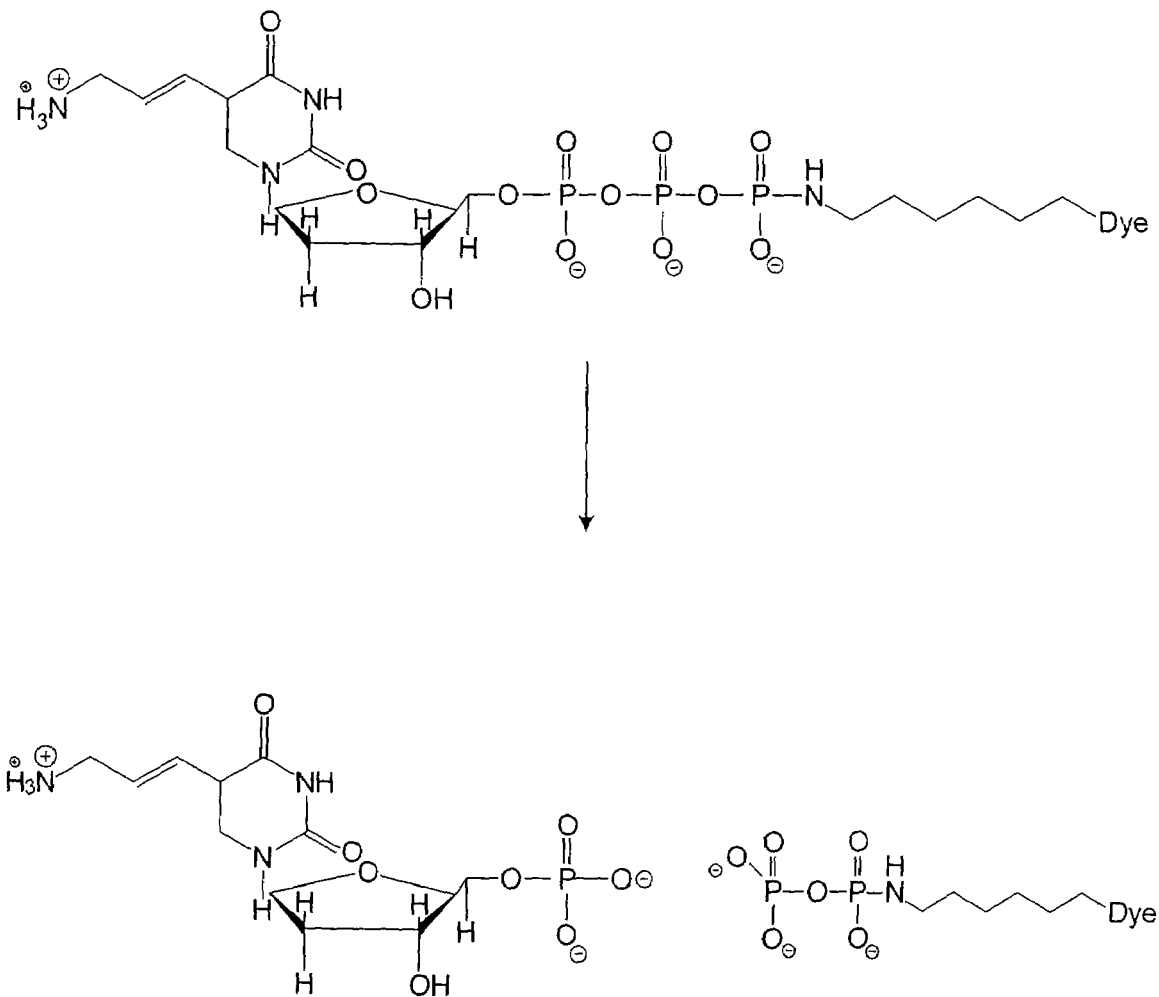
FIG. 1 illustrates a model compound of the present invention.

The term "charge-switch nucleotide" as used herein refers to a labeled nucleotide phosphate (e.g., γ-NP-Dye) that upon release or cleavage of a phosphate detectable moiety (e.g., PPi-Dye) has a different net charge associated with the cleavage product compared to the intact nucleotide phosphate probe (e.g., γ-NP-Dye). In certain preferred aspects, the attachment of the dye to the PPi is via a nitrogen in lieu of an oxygen.

Preferably, the charge difference between the intact γ-NP-Dye and the PPi-Dye is at least 0.5, and more preferably about 1 to about 4 (e.g., 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0).

The terms "PPi-Dye" or "PP-F" and the like, refer to the pyrophosphate cleavage product from an intact charge-switch nucleotide (NTP). If a nucleotide diphosphate is used, the cleavage product will be a "P-Dye" or "P-F".

The phrase "phosphate detectable moiety" refers to a detectable cleavage product from a NP probe of the present invention. Examples include, but are not limited to, PPi-Dye, PP-F, P-Dye, a phosphate fluorophore moiety, a terminal phosphate fluorophore moiety, a detectable moiety, charged groups, electrically active groups, detectable groups, reporter groups, combinations thereof, and the like.

The term "heterogeneous" assay as used herein refers to an assay method wherein at least one of the reactants in the assay mixture is attached to a solid phase, such as a solid support.

The term "oligonucleotide" as used herein includes linear oligomers of nucleotides or analogs thereof, including deoxyribonucleosides, ribonucleosides, and the like. Usually, oligonucleotides range in size from a few monomeric units, e.g. 3-4, to several hundreds of monomeric units. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, and "T" denotes thymidine, unless otherwise noted.

The term "nucleoside" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g., as described in Kornberg and Baker, *DNA Replication*, 2nd Ed. (Freeman, San Francisco, 1992).

The term "nucleotide" as used herein refers to a phosphate ester of a nucleoside, e.g., mono, di and triphosphate esters, wherein the most common site of esterification is the hydroxyl group attached to the C-5 position of the pentose. Nucleosides also include, but are not limited to, synthetic nucleosides having modified base moieties and/or modified sugar moieties, e.g. described generally by Scheit, *Nucleotide Analogs* (John Wiley, N.Y., 1980). Suitable NTPs include both naturally occurring and synthetic nucleotide triphosphates, and are not limited to, ATP, dATP, CTP, dCTP, GTP, dGTP, TTP, dTTP, UTP and dUTP. Preferably, the nucleotide triphosphates used in the methods of the present invention are selected from the group of dATP, dCTP, dGTP, dTTP, dUTP and mixtures thereof.

The term "primer" refers to a linear oligonucleotide, which specifically anneals to a unique polynucleotide sequence and allows for synthesis of the complement of the polynucleotide sequence. In certain aspects, a primer is covalently attached to the template as a hairpin.

The phrase "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, or oligonucleotide, as well as the express identification and ordering of nucleosides, usually each nucleoside, in a target polynucleotide. The term also includes the determination of the identification, ordering, and locations of one, two, or three of the four types of nucleotides within a target polynucleotide.

The term "solid-support" refers to a material in the solid-phase that interacts with reagents in the liquid phase by heterogeneous reactions. Solid-supports can be derivatized with proteins such as enzymes, peptides, oligonucleotides and polynucleotides by covalent or non-covalent bonding through one or more attachment sites, thereby "immobilizing" the protein or nucleic acid to the solid-support.

The phrase "target nucleic acid" or "target polynucleotide" refers to a nucleic acid or polynucleotide whose sequence identity or ordering or location of nucleosides is to be determined using methods described herein.

The phrase "terminal phosphate oxygen" refers to the secondary ionization oxygen atom (pK ~6.5) attached to the terminal phosphate atom in a nucleotide phosphate probe.

The phrase "internal phosphate oxygen" refers to the primary ionization oxygen atoms (pK ~2) in a nucleotide phosphate probe. An NTP has 3 internal phosphate oxygens (one each on the $\alpha$, $\beta$, and $\gamma$-phosphates) plus 1 terminal phosphate oxygen (on the $\gamma$-phosphate).

The phrase "single molecule configuration" refers to the ability of the compounds, methods and systems of the present invention to measure single molecular events, such as an array of molecules on a solid support wherein members of the array are present as individual molecules located in a defined location. The members can be the same or different.

II. Compounds

In one embodiment, the present invention provides a charge-switch nucleotide phosphate (NP) probe. The NP probe has a terminal phosphate with a fluorophore moiety attached thereto. The NP probe can be a nucleotide diphosphate or nucleotide triphosphate. Preferably, the charge-switch NP probe is a nucleotide triphosphate. In certain preferred aspects, the nucleoside moiety is modified with adducts to confer positive or negative charge. As explained in detail below, modification can occur at the base, the sugar, the phosphate group, linkers and combinations thereof. Advantageously, by electrically sorting molecules having different charges relative to each other, such as by separating an intact charge switch nucleotide from its cleaved PPi-Dye, the cleaved PPi-Dye (PPi-F) molecules are detected in isolation without interference from unincorporated NP probes (e.g., $\gamma$-NP-Dye).

In certain embodiments, the incorporation of an NP probe in the growing complementary strand of nucleic acid results in release of a phosphate detectable moiety. In a preferred embodiment, the detectable moiety is a $\gamma$-phosphate label that is cleaved from $\gamma$-labeled dNTPs by a polymerase. In an especially preferred embodiment, $\gamma$-labeled-dNTPs having a cationic $\gamma$-label exhibit charge-switching behavior, wherein the electric charge of the intact triphosphate ($\gamma$-NTP-Dye) is negative while the released PPi-Dye is positive. Thus, the release of the PPi-Dye results in a cleavage-dependent charge alteration to the PPi-fluorophore moiety. In certain aspects, cleavage of pyrophosphate from the nucleoside subtracts charges associated with the nucleoside. These charge changes can be either positive or negative. In certain aspects, the cleavage of the PPi-Dye adds a positive charge to the PPi-Dye moiety by generating a terminal phosphate oxygen, as a terminal phosphate-oxygen binds mono or divalent cations (e.g., $Mg^{++}$, $Mn^{++}$, $K^+$, $Na^+$ and the like) as counter ions, better than an internal phosphate-oxygen.

In certain aspects, the charge-switch NP probes of the present invention have a net positive charge. For example, the base can have an amine attached thereto and this amine can be protonated. Upon cleavage of the base-cation, the PPi-Dye becomes more negative. Conversely, cleavage of a negative-base NP (e.g., a base with a carboxylate, sulfonate, and the like attached thereto) makes the PPi-Dye more positively charged. Cleavage of a neutral-base NTP (natural structure), will have no contribution to the PPi-Dye other than generation of a terminal phosphate oxygen.

A. Charge State

The charge state of the NP probe as well as the released terminal phosphate (e.g., pyrophosphate) are parameters of the compounds of the present invention. Those of skill in the art will appreciate the various parameters making-up or contributing to the charge on the $\gamma$-NP-Dye and the terminal phosphate-Dye (e.g., PPi-Dye moiety). In certain aspects, a charge-switch nucleotide phosphate (NP) probe comprises an intact NP probe having a terminal phosphate with a fluorophore moiety attached thereto. The intact NP probe has a first molecular charge associated therewith; and whereupon cleavage of the terminal phosphate such as cleavage of a pyrophosphate fluorophore moiety, the pyrophosphate fluorophore moiety carries a second molecular charge. The first molecular charge is different than the second molecular charge by at least 0.4 as calculated under ionic conditions obtained in pure water, at about pH 7 (see, FIG. 2). The charge difference between the intact NP probe is more preferably between about 1 and about 4, and any fraction of the integers 1, 2, and 3.

The charge state of the either the $\gamma$-NP-Dye or terminal phosphate-Dye (e.g., PPi-Dye) or both can be determined for any ionic condition by calculating the i) charge on the base; the ii) charge on the fluorophore or linker; and iii) the buffer cation composition and concentration (see, Example I).

In general, the net electric charge on a nucleotide phosphate such as a dNTP, is governed by the base ring nitrogens and by the three phosphates. At a pH from about 6.5 to about 8.5, the bases are mostly uncharged (nitrogen pK of 3-4 and 9.5-10). The primary ionization of each ionizable oxygen atom on each phosphate (pK ~2) contributes one full negative charge. The secondary ionization specific to the phosphate oxygen (pK ~6.5) contributes a time-averaged charge of –0.9 at pH 7.5 so the total charge on the dNTP is –3.9.

FIG. 1 illustrates a representative compound of the present invention showing an intact $\gamma$-NP-Dye and the released pyrophosphate having a detectable moiety. As shown therein, in certain aspects, the nucleobase carries a cationic adduct and the terminal oxygen is replaced by a nitrogen and a label moiety in a $\gamma$-dNTP, thus, the secondary ionization is eliminated and at pH 7 ($H_2O$), the charge on a $\gamma$-dNTP is –2.0 (for a neutral $\gamma$-label). After cleavage from the nucleotide, the charge on the PPi-Dye is –2.74, because it has lost the positive charge (+1) of the nucleobase, but has gained back a partial positive charge (+0.26) due to hydrogen ion equilibration with the terminal phosphate oxygen (pK 6.4 secondary ionization of substituted diphosphates).

FIG. 2 is a look-up table showing various embodiments and charges associated with the nucleobase and dye and their respective net charges under ideal conditions (without associated counter ions or buffers; charged adducts fully charged) or in pure water (last column only). Entry 32 illustrates the preceding example. As tabulated therein, for ideal conditions, the nucleobase has a charge of 1, the dye has a charge of 0 and therefore a net charge of –2 is associated with the $\gamma$-NP-Dye and a charge of –3 for the PPi-Dye, giving a charge difference of –1. The charge difference is slightly less (–0.74; last column) in pure water at pH 7, however, because the terminal phosphate oxygen of PPi-F associates more readily with hydrogen ions. As shown therein, various electric charges placed on the nucleobase and the dye will have different effects on the dye upon incorporation of the nucleobase into a growing nucleic acid. The charge difference under ideal conditions is equal to the sum of the opposite of the charge on the nucleobase moiety and the terminal phosphate dye moiety, as the nucleobase is separated from the dye when the nucleobase is incorporated into DNA. The charge difference in pure water (last column) takes into account hydrogen ion equilibrium binding.

In certain other embodiments, the charge-switch NP probes of the present invention have various counter ions associated with them (e.g., $Mg^{++}$ or other cations). For example, $Mg^{++}$ binds to phosphate groups in a variety of coordination isomers that rapidly equilibrate at $10^3$ to $10^5$ $sec^{-1}$. $Mg^{++}$ ions, like protons, bind more tightly to terminal phosphates than to "internal" phosphates, meaning that a PPi-Dye moiety acquires more positive charge from the counter ions than a γ-dNTP-Dye. In operation, this difference is utilized to sort or separate the released PPi-Dye from the intact γ-NTP-Dyes in for example, a microchannel system using the compounds, methods and systems of the present invention.

As explained in more detail below, the magnitude of a charge-switch can be enhanced by attaching positive or negative charged groups to the nucleoside (normally neutral at pH 7.5). The range of the charge-switch can be set by attaching charged groups to the γ-phosphate label, either on the fluorophore and/or linker, such that both the NP probe and the PPi-F are negatively charged, or both are positively charged, or one is negative while the other is positive. All such combinations and permutations are encompassed by the present invention. Thereafter, when the base is incorporated into DNA, the charged group is separated from the PPi-F to enhance the "natural" counter ion (e.g., $Mg^{++}$) dependent charge effect.

There are 10 charge-switch modes that can be exploited for sorting (neg to weak neg, neg to strong negative, neg to zero, neg to pos, zero to neg, zero to pos, pos to neg, pos to zero, weak to strong pos and strong to weak pos). The two "bipolar" modes i.e., negative to positive, positive to negative are preferred for electrosorting, although the other modes can also be used under appropriate microfluidic conditions. Other preferred compounds from FIG. 2 are set forth in Table 1.

TABLE 1

| Compound | Charges |
|---|---|
| 20 | N(−1) F(+2) |
| 13 | N(−2) F(+2) |
| 12 | N(−2) F(+1) |
| 40 | N(+2) F(+1) |
| 39 | N(+2) F(0) |
| 19 | N(−1) F(+1) |
| 27 | N(0) F(+2) |
| 33 | N(+1) F(+1) |
| 26 | N(0) F(+1) |
| 41 | N(+2) F(+2) |

Figure 3:
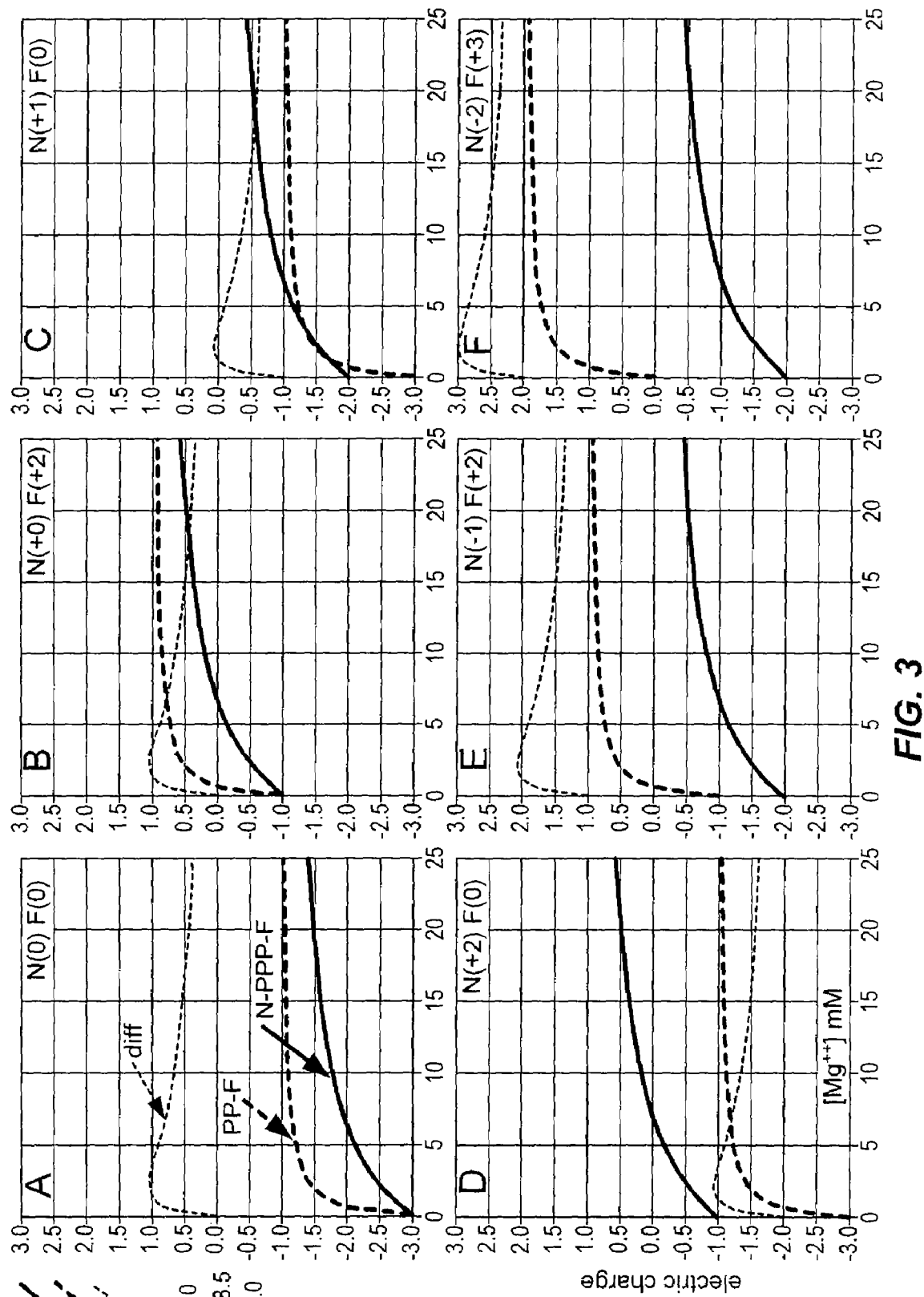
FIG. 3 (A-F) illustrates schematically equilibrium calculations showing the effect of $Mg^{+-}$ on the time-averaged electric charge on the "ligands" N-PPP-F and PP-F (N=nucleotide, PPP=triphosphate, PP=pyrophosphate, F=γ-label). Binding to the ions $H^+$ and $Mg^{++}$ are considered. The fraction of ligand bound to an ion, fracBound, is given as fracBound=[ion]/([ion]+K), where K is the ion concentration giving fracBound=50% (i.e., the association or dissociation constant). The fractions of N-PPP-F and PP-F in protonated form were calculated according to the above eqn. Then, the fraction bound to $Mg^{++}$ was calculated for both the protonated and unprotonated forms of N-PPP-F and PP-F. The average charge was then calculated by multiplying the fraction of each form by its respective charge and adding all of the forms of the molecule. Results are plotted as a function of $Mg^{++}$ concentration (0-25 mM). Charges on N and F were modeled as pH-independent quaternary salts (+) or carboxylates (−) PANEL A N(0) F(0), PANEL B N(0) F(2), PANEL C N10) F(0), PANEL D N(2) F(0), PANEL E N(−1) F(2), PANEL E N(−2) F(3)

In order to obtain a bipolar mode, the γ-dNTP is "poised" with respect to charge so that the charge switch "passes through" neutral. FIG. 3 (A-F) illustrate how the counter ion concentration (e.g., $Mg^{++}$ ion) affects the charge of a generic γ-nucleotide (N—PPP-F) and a cleavage product (PP-F). Six different charge configurations "N(b) F(g)" are shown (A-F) wherein b and g are the charge on the nucleoside or γ-label, respectively. The charged groups (having different pK's) can be for example, primary or quaternary amines which add positive charge (+), or a carboxylic acid, which adds negative charge (−) and the like. With no added groups N(0) F(0) (Panel A), the maximum charge switch at pH 8 ($\Delta q=+1$) occurs at about 2 mM $Mg^{++}$, with the change being in negative range (−2.5 to −1.5). By adding a charge of (+2) to the γ-label (Panel B), the same switch magnitude is obtained ($\Delta q=+1$), except now the shift is a bipolar mode wherein the γ-dNTP-F and PPi-F are oppositely charged (−0.5 to +0.5).

Other configurations in FIG. 3 (C-F) show how the charge switch magnitude can be further increased (to facilitate electrosorting) by adding various charges to the nucleobase and/or γ-label. As is apparent from FIG. 3, the charge difference ($\Delta q$) can occur in negative range, positive range, negative to positive range or positive to negative range.

Figure 4:
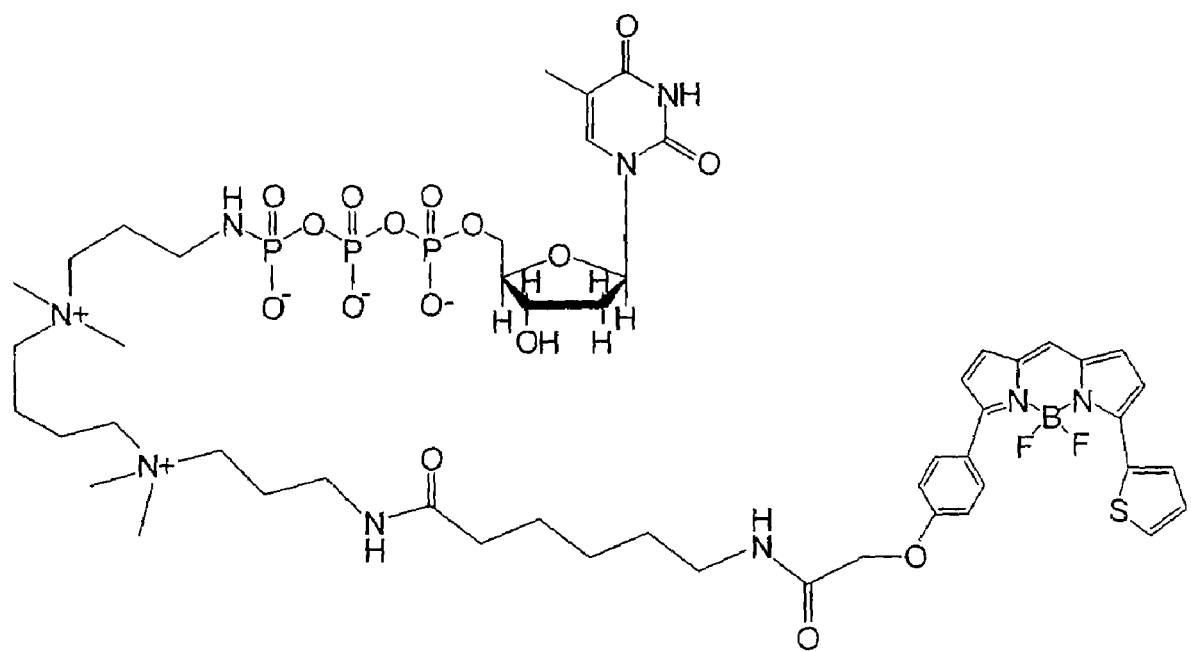
FIG. 4 illustrates a compound of the present invention (dTTP-BQS-BTR)

As exemplified in FIG. 4, the charge difference between the intact NP probes and the detectable moieties can be introduced via a charged moiety fixed to the γ-label such that, the γ-NTP-Dye is net negative, while the PPi-Dye is net positive. As shown therein, the electroneutral dye BODIPY®TR is conjugated to dTTP using a linker having a charge of +2. This nucleotide can be incorporated into DNA by a polymerase, with the release of phosphate, thus the PPi-Linker-Dye moiety acquires a more positive charge than the intact γ-NTP-Dye.

Using the equations set forth in Example I below, and with reference to FIG. 5, it is possible to calculate the net charge on the γ-NP-Dye and the released terminal phosphate (e.g., PPi-Dye) in the presence and absence of a metal counter ion. In certain instances, equilibrium association of cations to the compounds of the present invention will add about 1 positive charge to $\Delta q$, depending on the cation composition, concentration and pH (see, FIG. 3).

Figure 5:
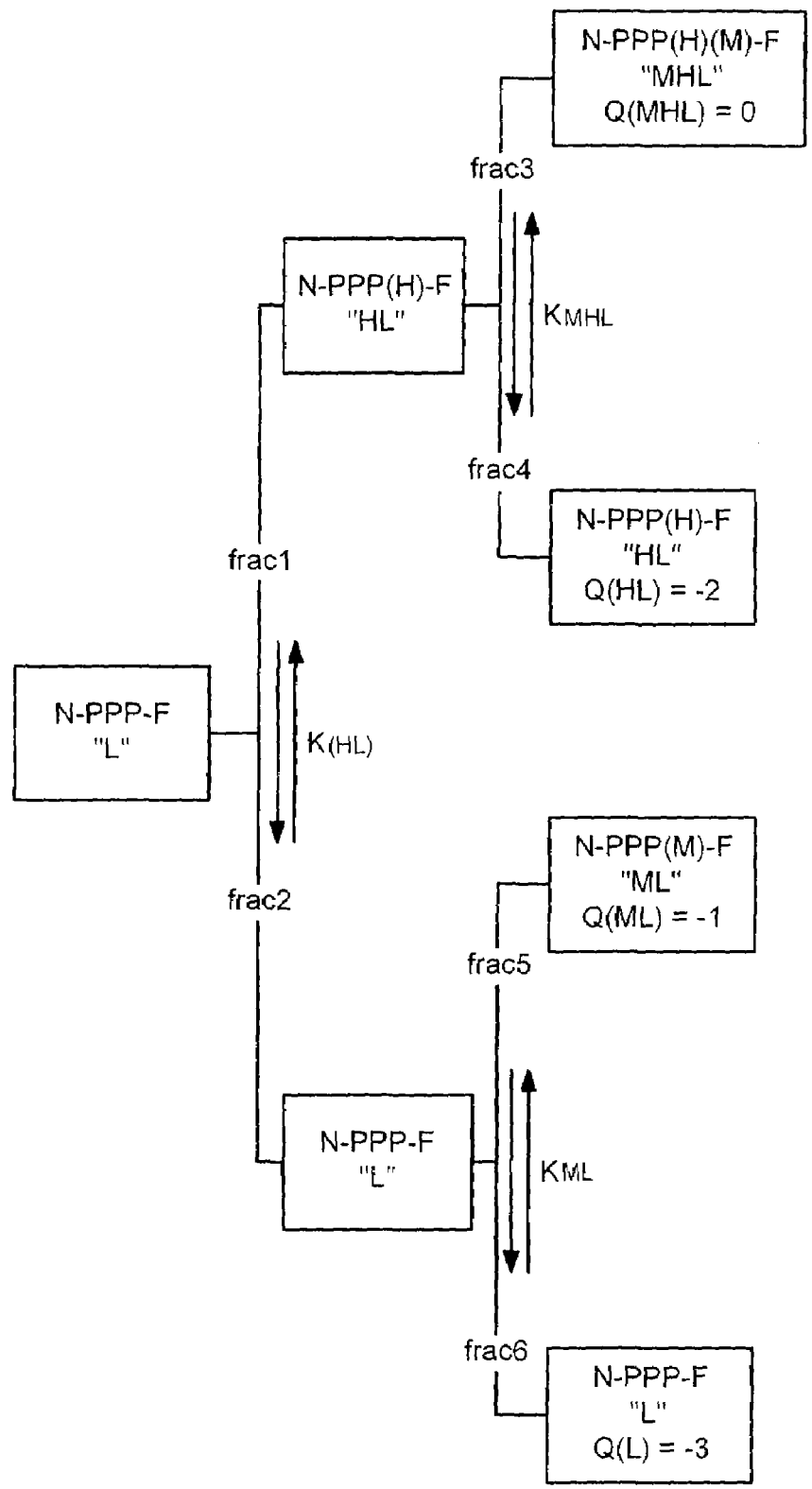
FIG. 5 illustrates a schematic of equilibrium calculations of the present invention (see, Example I)

The determination of charge on each moiety can be carried out using the equilibrium calculations in Example I below and as illustrated in FIG. 5. Using the equilibrium equations, Example I sets forth the charge determination of the compound in FIG. 4.

Figure 6E:
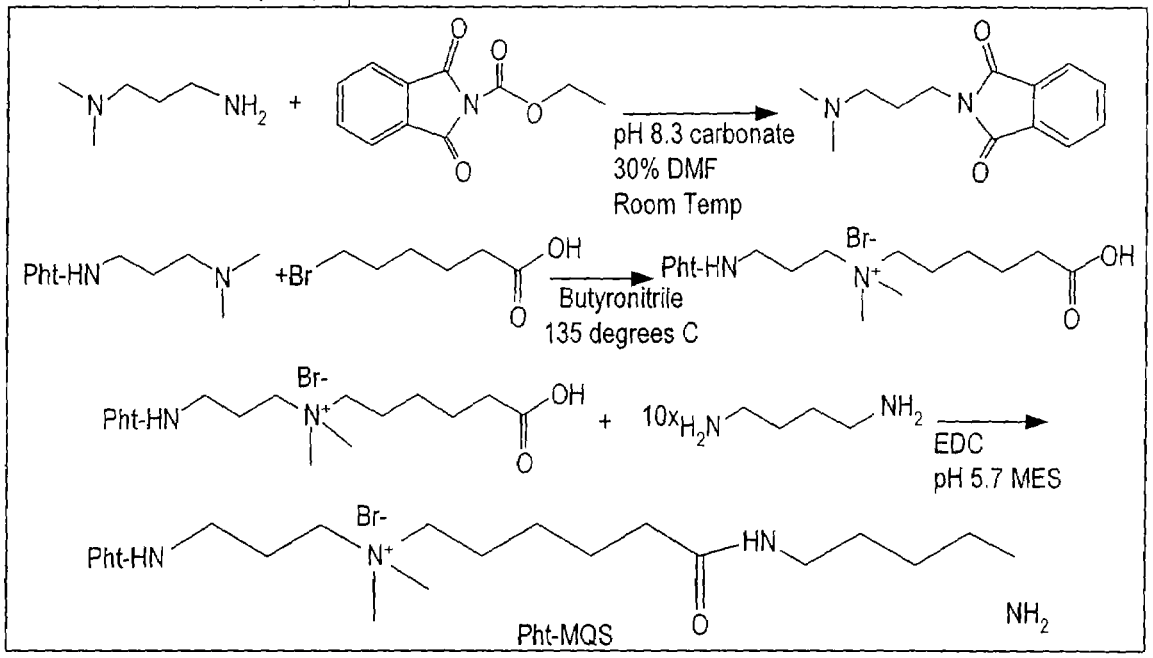
FIG. 6 (A-F) PANEL A compounds of the present invention; PANEL B compounds of the present invention; PANEL C compounds of the present invention; PANEL D compounds of the present invention; PANEL E various linker embodiments used in compounds of the present invention; and PANEL F various linker embodiments used in compounds of the present invention.
Figure 6E:
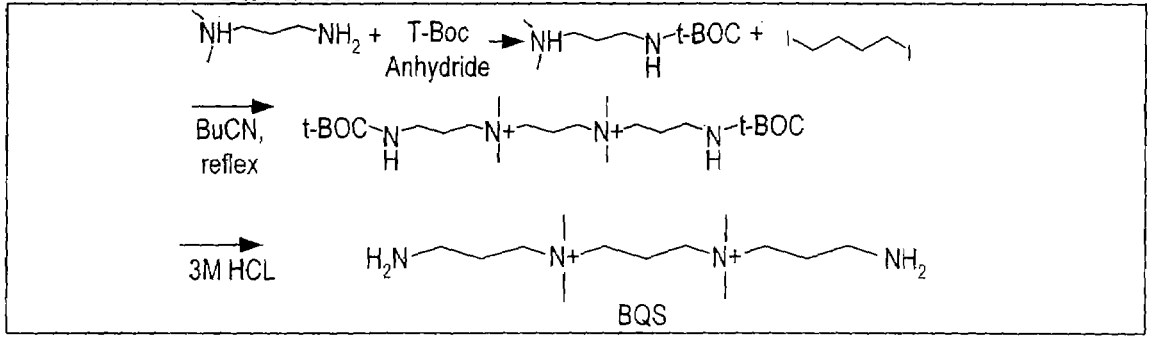
Figure 6E:
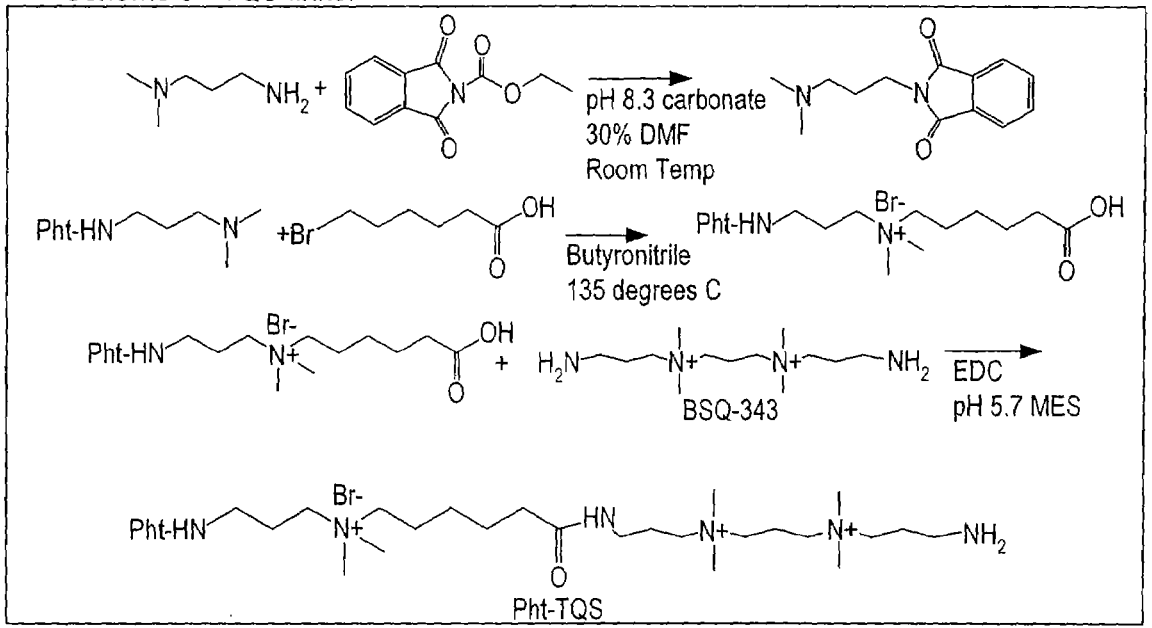

FIG. 6 (A-D) illustrates various charge-switch nucleotides of the present invention. These compounds are merely an illustration and should not limit the scope of the claims herein. One of ordinary skill in the art will recognize other variations, modifications, and alternatives.

In certain aspects, the present invention provides a charge-switch nucleotide phosphate (NP) probe. The NP probe has a terminal phosphate with a fluorophore moiety attached thereto, wherein the intact NP probe has a first molecular charge associated therewith, and upon cleavage of the fluorophore moiety having a phosphate or pyrophosphate group appended thereto, the P-F or PPi-F has a second charge. The first charge and second charge are different. Formula I provides charge-switch nucleotide phosphate probes of the present invention:

I

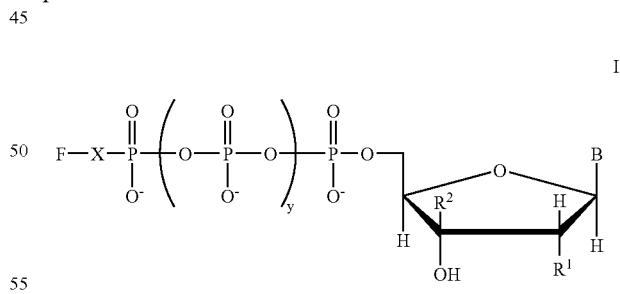

In Formula I, B is a nucleobase including, but not limited to, naturally occurring or synthetic purine or pyrimidine heterocyclic bases, including but not limited to adenine, guanine, cytosine, thymine, uracil, 5-methylcytosine, hypoxanthine or 2-aminoadenine. Other such heterocyclic bases include 2-methylpurine, 2,6-diaminopurine, 6-mercaptopurine, 2,6-dimercaptopurine, 2-amino-6-mercaptopurine, 5-methylcytosine, 4-amino-2-mercaptopyrimidine, 2,4-dimercaptopyrimidine and 5-fluorocytosine. Representative heterocyclic bases are disclosed in U.S. Pat. No. 3,687,808 (Merigan, et al.), which is incorporated herein by reference.

In certain preferred aspects, B comprises a charged moiety. These charged base-moieties can be positively or negatively charged. Using a charged base-moiety, it is possible to impart additional charge onto the base or the intact 7-dNTP-F. Suitable charged base linking groups can append carboxylic acid group, sulfonic acid group, and the like.

$R^1$ in Formula I is a hydrogen, a hydroxyl group or charged group e.g., L-$SO_3^-$, L-$NH_3^+$, L-$CO_2^-$ and the like; wherein L is a linker.

$R^2$ in Formula I is a hydrogen, or charged group e.g., L-$SO_3^-$, L-$NH_3^+$, L-$CO_2^-$ and the like; wherein L is a linker.

In Formula I, X is a heteroatom such as nitrogen, oxygen, and sulfur. Preferably, X is nitrogen. As the NP probes of the present invention can be tetraphosphates, triphosphates or diphosphates, the index "y" in Formula I, can be 0, 1 or 3.

In Formula I, F is a fluorophore or dye. In certain preferred aspects, F comprises a charged label linker group. Using the charged label linking group, it possible to impart additional charge onto the fluorophore moiety (i.e., the cleaved PPi-F or P-F). Suitable charged label-linking groups can append quaternary nitrogens and the like. The compounds of Formula I can have counter ions associated therewith. These counter ions include mono and divalent metal ions including, but are not limited to, $Mg^{++}$, $Mn^{++}$, $K^+$ and $Na^+$. Those of skill in the art will know of additional counter ions suitable for use in the present invention. FIGS. 6(A-D) set forth preferred compounds of the present invention.

B. Labels

Many dyes or labels are suitable for charge-switch nucleotide phosphates of the present invention. In fact, there is a great deal of practical guidance available in the literature for providing an exhaustive list of fluorescent and chromogenic molecules and their relevant optical properties (see, for example, Berlman, *Handbook of Fluorescence Spectra of Aromatic Molecules*, 2nd Edition (Academic Press, New York, 1971); Griffiths, *Colour and Constitution of Organic Molecules* (Academic Press, New York, 1976); Bishop, Ed., Indicators (Pergamon Press, Oxford, 1972); Haugland, *Handbook of Fluorescent Probes and Research Chemicals* (Molecular Probes, Eugene, 1992) Pringsheim, *Fluorescence and Phosphorescence* (Interscience Publishers, New York, 1949); and the like. Further, there is extensive guidance in the literature for derivatizing fluorophore molecules for covalent attachment via common reactive groups that can be added to a nucleotide, as exemplified by the following references: U.S. Pat. No. 3,996,345; Khanna et al., and U.S. Pat. No. 4,351,760.

In certain preferred aspects, suitable dyes include, but are not limited to, coumarin dyes, xanthene dyes, resorufins, cyanine dyes, difluoroboradiazaindacene dyes (BODIPY), ALEXA dyes, indoles, bimanes, isoindoles, dansyl dyes, naphthalimides, phthalimides, xanthenes, lanthanide dyes, rhodamines and fluoresceins. In certain embodiments, certain visible and near IR dyes are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the present invention.

In certain preferred aspects, suitable dyes include, but are not limited to, fluorescein, 5-carboxyfluorescein (FAM), rhodamine, 5-(2'-aminoethyl)aminonapthalene-1-sulfonic acid (EDANS), anthranilamide, coumarin, terbium chelate derivatives, Reactive Red 4, BODIPY dyes and cyanine dyes.

In certain aspects, the phosphate detectable moiety is a charged group. As explained below, Schemes 1-6 in FIG. 6 E sets forth aliphatic linkers for γ-phosphate conjugation. In certain aspects, the linkers in Schemes 1-6 can be used without further attachment of a label such as a fluorophore. The linkers themselves can be used as the phosphate detectable moieties.

C. Linkers to the Label

There are many linking moieties and methodologies for attaching fluorophore moieties to nucleotides, as exemplified by the following references: Eckstein, editor, *Oligonucleotides and Analogues: A Practical Approach* (IRL Press, Oxford, 1991); Zuckerman et al., *Nucleic Acids Research*, 15: 5305-5321 (1987) (3' thiol group on oligonucleotide); Sharma et al., *Nucleic Acids Research*, 19: 3019 (1991) (3' sulfhydryl); Giusti et al., *PCR Methods and Applications*, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); AP3 Labeling Technology (U.S. Pat. Nos. 5,047,519 and 5,151,507, assigned to E.I. DuPont de Nemours & Co); Agrawal et al., *Tetrahedron Letters*, 31: 1543-1546 (1990) (attachment via phosphoramidate linkages); Sproat et al., *Nucleic Acids Research*, 15: 4837 (1987) (5' mercapto group); Nelson et al., *Nucleic Acids Research*, 17: 7187-7194 (1989) (3' amino group); and the like.

In certain aspects, the fluorophore moiety is a fluorescent organic dye derivatized for attachment to a γ-phosphate directly or via a linker. In general, nucleotide labeling can be accomplished using any of a large number of known nucleotide labeling techniques using known linkages, linking groups, and associated complementary functionalities. The linkage linking the fluorophore to the phosphate should be compatible with relevant polymerases.

In one embodiment, the linker is an alkylene group, such as a methylene or ethylene group. In this embodiment, the fluorophore linker is an alkylene group having between about 1 to about 50 carbon atoms, preferably about 10 to 30 carbon atoms and more preferably, about 15 to about 25 carbon atoms, optionally interrupted by heteroatom(s). In certain aspects, the linker has at least 1 positive or negative charge associated therewith.

In certain other embodiments, various charged linkers can also be used. Schemes 1-6 in FIG. 6 E sets forth aliphatic linkers for γ-phosphate conjugation.

As shown therein, Scheme 1 sets forth a MQS(+) (monoquaternary salt) linker generated using a phthaliamide protecting group. The MQS is thereafter used as a reagent in Schemes 3 and 4. Scheme 2 sets forth a BQS(++) (bisquaternary salt) linker. Scheme 3 sets forth a TQS(+++) (triquaternary salt) linker, which is made by combining one MQS unit with one BQS unit using appropriate stoichiometry. The phthaliamide protecting group is removed when necessary in 1M NaOH for 2 h. In addition, Scheme 4 sets forth a TetQS (++++) (tetraquaternary salt) linker made by combining two MQS units with one BQS unit as shown. Scheme 5 sets forth protection of the aminoally amino group of AA-dUTP, and Scheme 6 sets forth the chemistry to couple the BQS linker to dTTP. The product is purified by HPLC and reacted with the succinimide ester of BodipyTR.

In still other embodiments, FIG. 6F sets forth peptide moieties for linking the fluorophore to the terminal phosphate. Preferably, the peptide is between 2 and 15 amino acids in length. Scheme 7 shows the coupling of 3 lysines (KKK) through their ε-amines so that each residue provides 7 atoms to the linker. The three lysines together form a largely-aliphatic linker 21 atoms long, about the same size as the BQS linker. Both the C and N-termini of the peptide are blocked by amidation or acylation. A reversible protecting group is required to achieve directional coupling. Using a protecting group having the sequence RPTL (C—N direction), it is possible to cleave the peptide linker very specifically by thrombin on the C-terminal side of the arginine (Harris et al., *Proc Nat Acad Sci USA*, 97:7754-7759 (2000)). In addition, Scheme 8 shows the peptides of Scheme 7 being coupled directionally to the γ-P of dNTPs. Additional linkers suitable for use in the present invention will be apparent to those of skill in the art.

D. Charged Moieties on the Base

In certain aspects, the base has a charged moiety appended thereto to increase or decrease molecular charge. In general, attaching one or more nucleotide charged moieties can be accomplished using any of a large number of known nucleotide labeling techniques using known linkages, linking groups, and associated complementary functionalities. Preferably, the linkage attaching the charged moiety and nucleotide should be compatible with relevant polymerases.

Preferably, the charged moieties are covalently linked to the 5-carbon of pyrimidine bases and to the 7-carbon of 7-deazapurine bases. Several suitable base labeling procedures have been reported that can be used with the present invention, e.g. Gibson et al., *Nucleic Acids Research*, 15: 6455-6467 (1987); Gebeyehu et al., *Nucleic Acids Research*, 15: 4513-4535 (1987); Haralambidis et al., *Nucleic Acids Research*, 15: 4856-4876 (1987); Nelson et al., *Nucleosides and Nucleotides*, 5(3) 233-241 (1986); Bergstrom, et al., *JACS*, 111, 374-375 (1989); U.S. Pat. Nos. 4,855,225, 5,231, 191, and 5,449,767, each of which is incorporated herein by reference. Preferably, the linkages are acetylenic amido or alkenic amido linkages, the linkage between the charged moiety and the nucleotide base being formed by reacting an activated N-hydroxysuccinimide (NHS) ester of the charged moiety with an alkynylamino- or alkenylamino-derivatized base of a nucleotide.

The synthesis of alkynylamino-derivatized nucleosides is taught by Hobbs et al. in European Patent Application No. 87305844.0; U.S. Pat. Nos. 5,047,519 and 5,151,507, assigned to E.I. DuPont de Nemours & Co; and Hobbs et al., *J. Org. Chem.*, 54: 3420 (1989), which are incorporated herein by reference. As taught therein, the alkynylamino-derivatized nucleotides are formed by placing the appropriate halodeoxynucleoside (usually 5-iodopyrimidine and 7-iodo-7-deazapurine deoxynucleosides and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodeoxynucleoside.

As taught in U.S. Pat. No. 5,047,519, which issued to Hobbs et al. on Sep. 10, 1991, the alkynylamino linkers have the structure:

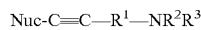

wherein $R^1$ is a substituted or unsubstituted diradical moiety of 1-20 atoms. Nuc is a purine or pyrimidine base. $R^1$ can be straight-chained alkylene, $C_1$-$C_{20}$, optionally containing within the chain double bonds, triple bonds, aryl groups or heteroatoms such as N, O or S. The heteroatoms can be part of such functional groups as ethers, thioethers, esters, amines or amides. Preferably, $R^1$ is straight-chained alkylene, $C_1$-$C_{20}$; most preferably $R^1$ is $CH_2$. Substituents on $R^1$ can include $C_1$-$C_6$ alkyl, aryl, ester, ether, amine, amide or chloro groups. $R^2$ and $R^3$ are independently H, alkyl, $C_1$-$C_4$, or a protecting group such as acyl, alkoxycarbonyl, a charged moiety or sulfonyl. Preferably $R^2$ is H, and $R^3$ is a charged moiety. The alkynylamino linker is preferably attached to the 5-position of the pyrimidine nucleotides and the 7 position of the purine nucleotides.

In still other embodiments, FIG. 6F sets forth methods for carboxylating the aminoally group of AA-dUTP using succinic anhydride (-1) or 1,2,4-benzenetricarboxylic anhydride (-2). This provides negatively charged bases to test the high-magnitude charge-switch configurations. In addition, Scheme 10 shows peptide linkers are used to synthesize the carboxylated γ-dUTPs mentioned in Scheme 9.

In yet another aspect, the charge group is attached to the sugar. Suitable charged groups and their syntheses are disclosed in U.S. Pat. No. 6,191,266 (incorporated herein by reference). The charged groups can be at C-2 or C-3 or combinations thereof.

E. Assay to Assess Charge

Those of skill in the art will readily recognize that various assays are easily implemented to assess the charge of the intact nucleotide phosphate and the cleaved pyrophosphate carrying a label. The following assay is just one of many available assays to calculate and assess the net charge on the γ-NP-Dye and the released PPi-F or P-F moiety.

In certain instances, the assay set forth in Example VII is used to test for a change in the electric charge associated with a dye attached to the terminal phosphate of a nucleotide. In one embodiment, the charge switch is caused by cleavage of a phosphodiester bond that links the dye to the nucleotide. In one example, cleavage is catalyzed by snake venom phosphodiesterase. It will be appreciated by those of skill in the art that other enzymes, such as a DNA polymerase listed herein, can also be used to demonstrate charge switching.

As such, in another embodiment, the present invention provides a method for identifying an intact charge-switch nucleotide phosphate (NP) probe, comprising: a) contacting a sample comprising the intact charge-switch NP probe with an enzyme to produce a phosphate detectable moiety; and b) applying an electric field to the sample, wherein the phosphate detectable moiety migrates to an electrode differently than the intact charge-switch NP probe.

III. Methods

The charge-switch nucleotide phosphate probes of the present invention can be used in a variety of methods and systems such as methods and systems for sequencing nucleic acid. As described above, in certain aspects, the γ-label is cleaved from γ-dNTPs by various polymerases. In this reaction, the phosphate ester bond between the α and β phosphates of the incorporated nucleotide is cleaved by the DNA polymerase, and the β-γ-diphosphate (pyrophosphate) is released in solution. As used herein, the term pyrophosphate also includes substitution of any of the oxygen atoms of the pyrophosphate group with a nitrogen or a sulfur atom or combinations thereof to generate thiopyrophosphate, dithiopyrophosphate, and the like. Separating the unincorporated γ-NP-Dyes from the PPi-Dye is facilitated when the unincorporated γ-NP-Dyes has a net charge that is different than the released PPi-Dye. For example, a cationic PPi-Dye and a negative intact γ-NP-Dyes (e.g., triphosphate) exhibit charge switching. This characteristic is useful for single-molecule DNA sequencing in a microchannel sorting system for example, where a polymerase-DNA complex is immobilized just upstream from a channel intersection.

A. Separating, Sorting and Sequencing

Figure 7:
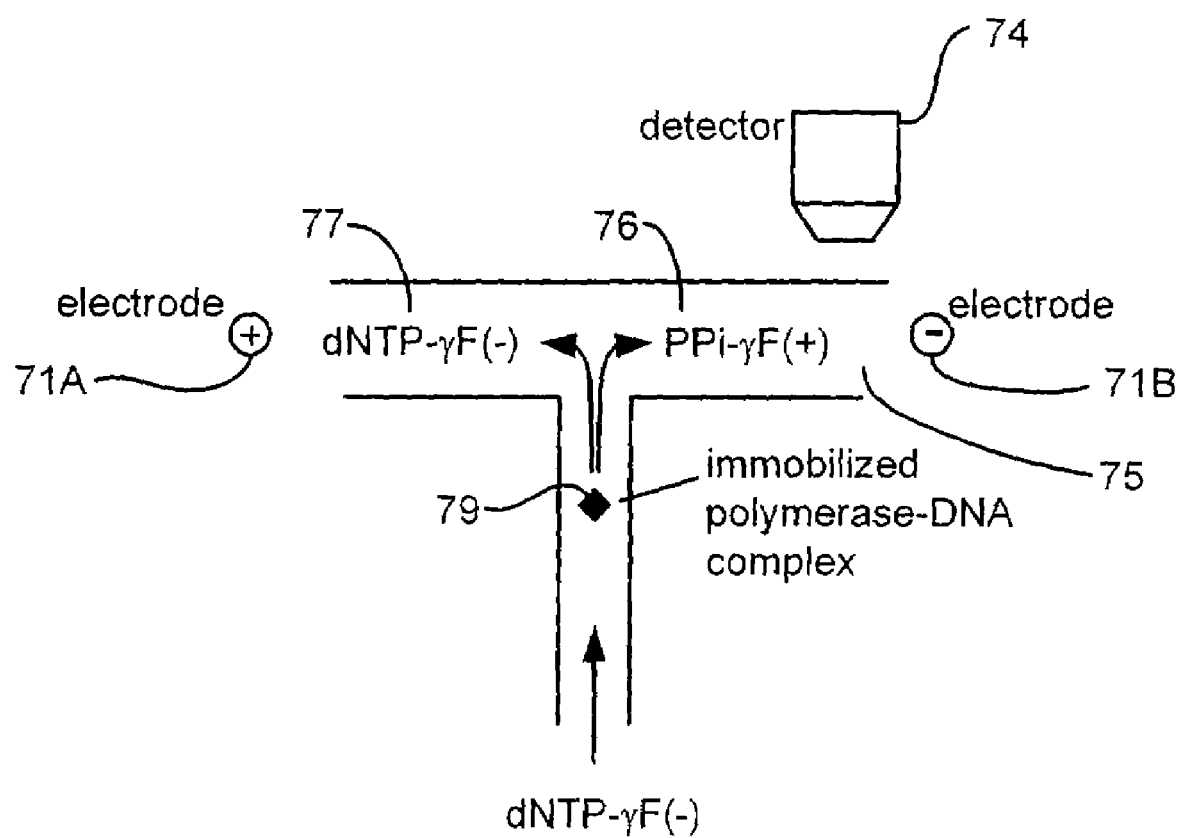
FIG. 7 illustrates a schematic of an embodiment of microfabricated flowcell of the present invention.

FIG. 7 is a schematic of a fabricated flowcell system 70 of the present invention. This diagram is merely an illustration and should not limit the scope of the claims herein. One of ordinary skill in the art will recognize other variations, modifications, and alternatives.

An electric field 71A and 71B at the intersection drives intact γ-dNTP-Dyes into a first microchannel toward the anode 71A, while PPi-Dye molecules are driven toward the cathode 71B into a second channel where they are detected with a detector 74. In operation, each of the 4 dNTPs is labeled with a different dye, enabling real-time sequencing as successive PPi-γ-Dye molecules flow through the detection channel 75. By electrically sorting differently-charged molecules in this manner, the cleaved PPi-Dye molecules 76 are detected in isolation without interference from unincorporated γ-dNTP-Dyes 77 and without illuminating the polymerase-DNA complex 79.

In certain aspects, a change in charge sign (e.g., from −1 on the γ-dNTP-Dye to +1 on the PPi-Dye) is utilized to separate the γ-dNTP-Dye from the PPi-Dye. In certain aspects, the γ-dNTP-Dye flows across a polymerase located just upstream from a transverse channel. The γ-dNTP-Dye is hydrolyzed by a polymerase and the liberated PPi-Dye diffuses into the medium and moves towards the transverse channel. A transverse electric field directs the PPi-Dye toward the negative electrode 71B, while the intact γ-dNTP-Dye molecules move toward the positive electrode 71A. Thereafter, the PPi-Dye molecules are detected in the transverse channel. Advantageously, this embodiment reduces or eliminates background from intact γ-dNTP-Dye molecules, thus allowing the use of high γ-dNTP-Dye concentrations to drive the polymerase reaction.

As such, the present invention provides a method for separating a labeled nucleotide phosphate having a detectable moiety from a released charged detectable moiety in a sample stream, comprising: a) immobilizing a nucleic acid complex onto a solid support in a single molecule configuration; b) contacting the complex with a polymerase and a plurality of nucleotide phosphates, wherein at least one of the plurality of nucleotide phosphate has a detectable moiety, wherein the detectable moiety is released as a charged detectable moiety when the NP is incorporated into the primer nucleic acid; and c) applying an electric field to the sample stream, thereby separating the labeled NP from the charged detectable moiety.

In another embodiment, the present invention provides a method for sequencing a target nucleic acid comprising: a) immobilizing a nucleic acid polymerase onto a solid support in a single molecule configuration, wherein the solid support is disposed in a flowcell having an inlet port and an outlet port; b) contacting the solid support with a sample stream comprising a target nucleic acid, a primer nucleic acid and a detectable nucleotide phosphate wherein the sample stream flows through the flowcell; c) applying an energy field to the sample stream; and d) detecting the detectable nucleotide phosphate thereby sequencing the target nucleic acid. Optionally, the primer nucleic acid is attached to the target nucleic acid.

Suitable nucleobases include, but are not limited to, adenine, guanine, cytosine, uracil, thymine, deazaadenine and deazaguanosine. In a preferred embodiment, the NP probes are dNTP probes having charge switch characteristics. In other aspects, the nucleobase is immobilized on a solid support and the sample stream contains a polymerase.

In certain preferred embodiments, the intact NP probe has a first molecular charge associated therewith; and whereupon cleavage of the terminal phosphate as a terminal phosphate fluorophore moiety, the phosphate fluorophore moiety carries a second molecular charge, wherein the difference between the first molecular charge and the second molecular charge is preferably between 1 and 4. The charge-switch characteristics are implemented upon enzymatic cleavage of the terminal phosphate or pyrophosphate group.

In certain aspects, at least two energy fields are used. By using at least two energy fields, the signal/noise discrimination can be enhanced when designed in conjunction with the expected charge on the signal molecule versus the noise molecule. That is, the signal molecule (fluorescent phosphates) responds more strongly to a particular field if its charge magnitude exceeds that of the noise molecule (e.g. unincorporated fluorescently labeled nucleotides), or less strongly if its charge magnitude is less than that of the noise molecule.

Upon incorporation by a polymerase, the dNTP is hydrolyzed as usual and the liberated pyrophosphate-dye moiety diffuses into the surrounding medium. The free dye molecule is fluorescent and its appearance is imaged at video-rate under a microscope. A flowing stream sweeps the dye away from the parent DNA molecule. As the polymerase continues to move along the DNA, the nucleotide sequence is read from the order of released dyes. Sequencing proceeds quickly, as fast as the polymerase progresses along the DNA template.

In another embodiment, the present invention provides a method for separating an intact NP probe from a phosphate detectable moiety, comprising: a) providing a sample comprising an intact NP probe with a detectable moiety attached thereto, whereupon an enzymatic cleavage of the intact NP probe, which produces a phosphate detectable moiety, the phosphate detectable moiety carries a molecular charge which is different than the molecular charge of the intact NP probe; and b) applying an energy field to the sample, thereby separating the phosphate detectable moiety from the intact NP probe.

In still yet another embodiment, the present invention provides a method for sequencing a nucleic acid, comprising: providing a target nucleic acid, a primer strand, a polymerase, and a plurality of NP probes; mixing the target nucleic acid, the primer strand, the polymerase, the plurality of NP probes in a flowcell under conditions permitting target dependent polymerization of the plurality of NP probes, thereby providing a polymerization product; and separating the polymerization product by an energy field in the flowcell to provide a sequence of the target nucleic acid.

In yet another embodiment, the present invention provides a method for sequencing a nucleic acid comprising: providing a target nucleic acid, a polymerase priming moiety, a polymerase, and labeled NPs; mixing the target nucleic acid, the polymerase priming moiety, the polymerase and the labeled NPs under conditions permitting target dependent polymerization of the NPs, such conditions which are capable of providing a time sequence of labeled pyrophosphate products; separating by charge the phosphate detectable moieties products from unpolymerized labeled NPs; and, detecting over time the phosphate detectable moieties to provide a sequence of the target nucleic acid. In certain aspects, the method relates to multi-molecule DNA sequencing, as well as single color (multi-molecule or single-molecule) sequencing where four different NP's (all labeled with the same color) are sequentially introduced to the reaction site. In other aspects, two, three, or four-color sequencing can be used.

B. Detection of Pyrophosphate

In certain other embodiments, the present invention provides a heterogeneous assay for the detection of pyrophosphate. The detection of pyrophosphate is advantageous in a number of biological reactions. For example, in a DNA polymerase reaction, wherein the polymerase selects a single DNA molecule from solution and thereafter incorporates the nucleotide at the 3'-end of a primer strand, the natural consequence of such incorporation is the release of pyrophosphate. If the assay solution comprises the four deoxynucleotide triphosphates, each dNTP labeled with a different color of fluorescent dye attached to the γ-phosphate, it is then possible to sequentially record the activity of the polymerase operating on a target DNA. The nucleotide sequence of the target DNA can thereafter be read directly from the order of released dyes attached to the pyrophosphate.

In other embodiments, the present invention provides methods for detecting and identifying individual fluorogenic NP molecules such as dNTP molecules, as a polymerase incorporates them into a single nucleic acid molecule. In certain aspects, a fluorescent dye is attached to the γ-phosphate. As describe above, charged moieties are attached to the nucleobase to modulate a change in the electric charge associated with the dye upon hydrolysis by a polymerase.

As such, the present invention provides a method for detecting pyrophosphate cleavage, the components of the assay comprising a charge-switch NTP, a target nucleic acid, a primer nucleic acid and a polymerase, the method comprising: (a) flowing the labeled charge-switch nucleotide phosphate (NP) having a γ-phosphate with a fluorophore moiety attached thereto, past an immobilized component selected from the group consisting of the polymerase and the target nucleic acid; (b) incorporating the NP on a primer strand hybridized to the target nucleic acid using an enzyme and releasing the γ-phosphate with the fluorophore moiety attached thereto; and (c) detecting the fluorescent moiety thereby detecting pyrophosphate cleavage. In the methods of the present invention, either the polymerase or the target nucleic acid is attached to a solid phase, such as a solid support. Preferably, in the methods of the present invention, the nucleic acid is immobilized on a solid support.

In many of the embodiments herein, the methods of the present invention employ a DNA polymerase such as DNA polymerase I, II or III. In other aspects, suitable polymerases include, but are not limited to, a DNA dependent RNA polymerase and reverse transcriptase such as an HIV reverse transcriptase. Specific examples include, but are not limited to, T7 DNA polymerase, φ29 DNA polymerase, T5 DNA polymerase, *E. Coli* DNA polymerase I, T4 DNA polymerase, T7 RNA polymerase and Taq DNA polymerase. Those of skill in the art will know of other enzymes or polymerases suitable for use in the present invention. In certain aspects, the target nucleic acid is bathed in a flowing solution comprising: polymerase unlabeled, single-stranded DNA fragments hybridized to an oligonucleotide primer and a mixture of NTPs. Optionally, the primer can be attached to the immobilized target nucleic acid.

In certain aspects, detection of the phosphate detectable moiety (e.g., PPi-Dye) is accomplished using an enzyme coupled assay. PPi can be determined by many different methods and a number of enzymatic methods have been described in the literature (Reeves et al., (1969), *Anal. Biochem.*, 28, 282-287; Guillory et al., (1971), *Anal. Biochem.*, 39, 170-180; Johnson et al., (1968), *Anal. Biochem.*, 15, 273; Cook et al, (1978), *Anal. Biochem.* 91, 557-565; and Drake et al., (1979), *Anal. Biochem.* 94, 117-120). Those of skill in the art will know of other enzyme coupled assays suitable for use in the present invention.

In one embodiment, the use of a phosphatase enhances the charge-switch magnitude by dephosphorylating the PPi-F. In certain other aspects, it is preferred to use luciferase and luciferin in combination to identify the release of pyrophosphate since the amount of light generated is substantially proportional to the amount of pyrophosphate released which, in turn, is directly proportional to the amount of base incorporated. The amount of light can readily be estimated by a suitable light sensitive device such as a luminometer.

Luciferin-luciferase reactions to detect the release of PPi are well known in the art. In particular, a method for continuous monitoring of PPi release based on the enzymes ATP sulphurylase and luciferase has been developed by Nyren and Lundin (*Anal. Biochem.*, 151, 504-509, 1985) and termed ELIDA (Enzymatic Luminometric Inorganic Pyrophosphate Detection Assay). The foregoing method may be modified, for example, by the use of a more thermostable luciferase (Kaliyama et al., 1994, *Biosci. Biotech. Biochem.*, 58, 1170-1171). The preferred detection enzymes involved in the PPi detection reaction are thus ATP sulphurylase and luciferase.

Figure 8:
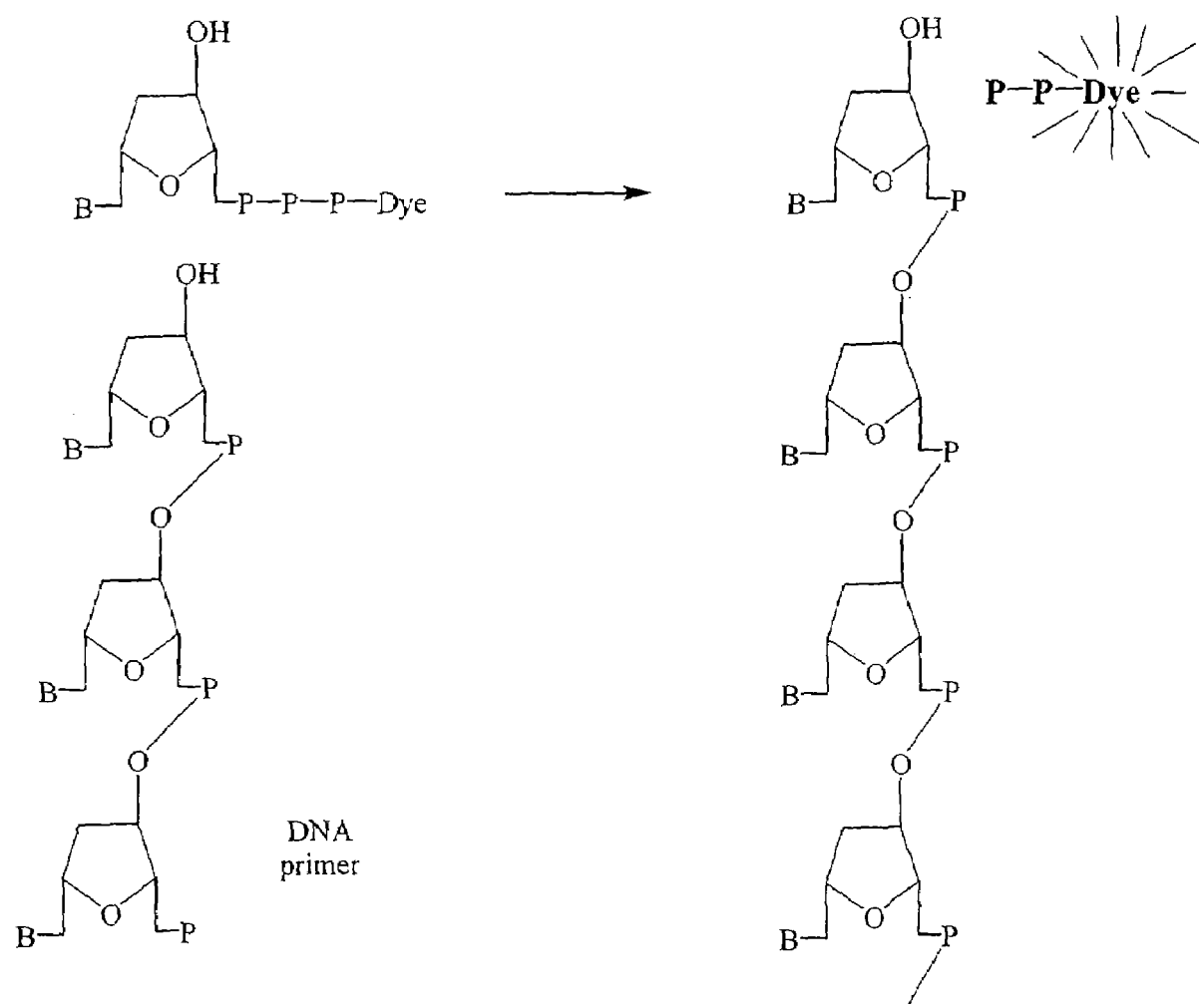
FIG. 8 illustrates a schematic of a method embodiment of the present invention.

As shown in FIG. 8, in preferred compounds of the present invention, wherein a fluorophore is attached to the γ-phosphate, the fluorophore is released from the nucleotide along with the pyrophosphate group. Using single molecule detection for example, fluorescent signals appear at the locations of the individual molecules being observed. In certain aspects, each type of nucleotide is labeled with a different fluorophore so that the incorporated nucleobases can be sequentially identified by the released fluorophores. Preferably, the nucleotide triphosphate (NTP) of the present methods include, but are not limited to, deoxyadenosine triphosphate, deoxycytosine triphosphate, deoxyguanosine triphosphate, deoxythymidine triphosphate, deoxyuridine triphosphate or mixtures thereof, each with a unique fluorophore attached to the γ-phosphate.

In certain embodiments, an unlabeled, single-stranded target nucleic acid with a primer hybridized thereto is tethered to the surface of a solid support such as a glass slide. In another aspect, a double stranded nucleic acid with a nick is tethered. An-aqueous solution comprising an enzyme, such as a DNA polymerase, and fluorogenic dNTPs flows across the surface. Alternatively, in another embodiment, an individual polymerase molecule is immobilized on a glass slide and the polymerase is bathed in a flowing solution comprising: 1) unlabeled, single-stranded DNA fragments hybridized to an oligonucleotide primer (or a covalently attached hairpin) and 2) a mixture of deoxynucleotide triphosphates, each uniquely labeled with a different color of fluorescent dye attached to the 7-phosphate.

In certain embodiments, an evanescent light field is set up by total internal refection (TIR) of a laser beam at the glass-aqueous solution interface. In certain aspects, the TIR illumination field is continuously imaged at video-rate with an intensified charge couple device (ICCD) camera.

C. Solid Phase

In certain embodiments herein, the present invention relates to methods wherein a material in the solid-phase interacts with reagents in the liquid phase. In certain aspects, the nucleic acid is attached to the solid phase. The nucleic acid can be in the solid phase such as immobilized on a solid support, through any one of a variety of well-known covalent linkages or non-covalent interactions. In certain aspects, the support is comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of the present invention, nucleic acid can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin are useful. Examples of other functional group linkers include ester, amide, carbamate, urea, sulfonate, ether, and thioester. A 5' or 3' biotinylated nucleotide can be immobilized on avidin or streptavidin bound to a support such as glass.

In other aspects of the methods of the present invention, the polymerase is immobilized on a solid support. Suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

In other aspects, polymerase immobilization is accomplished using solid chromatography resins that have been modified or activated to include functional groups that permit the covalent coupling of resin to enzyme. Typically, aliphatic linker arms are employed. The enzymes of the present invention can also be noncovalently attached to a solid support surface, through, for example, ionic or hydrophobic mechanisms.

In a preferred embodiment, covalent attachment of a protein or nucleic acid to a glass or metal oxide surface can be accomplished by first activating the surface with an amino silane. DNA or protein derivatized with amine-reactive functional groups can then attach to the surface (see, K. Narasimhan et al., *Enzyme Microb. Technol.* 7, 283 (1985); M. J. Heller et al., U.S. Pat. No. 5,605,662; and A. N. Asanov et al., *Anal. Chem.* 70, 1156 (1998)).

The ordinarily skilled artisan will know numerous other schemes for linking nucleic acid and proteins to support surfaces. Moreover, the choice of support surface and the method of immobilizing the enzyme is largely a matter of convenience and depends on the practitioner's familiarity with, and preference for, various supports surfaces, as well as preference for various immobilizing schemes, and knowledge of the substrate.

In operation, when the enzyme is immobilized, such as a DNA polymerase, the enzyme selects a single DNA molecule from solution. The polymerase incorporates a first nucleotide at the 3'-end of the primer strand. The polymerase then translocates to the next position on the target DNA, incorporates a complementary nucleotide, and releases the respective PPi-Dye. The released dyes move away from the immobilized enzyme in the flowing sample solution. These events can then be recorded sequentially by video-rate imaging using for example, a CCD camera, capable of detecting single fluorophore molecules. The resulting movie shows the activity of a single polymerase molecule operating on a single molecule of DNA. The nucleotide sequence of the DNA target is read directly from the order of released dyes. When the first nucleic acid molecule has been sequenced, the polymerase releases it and selects another template from solution. Many DNA molecules are thereby sequenced by a single polymerase. The process continues for the life of the enzyme.

D. Preparation of Target Nucleic Acid The target nucleic acid can be prepared by various conventional methods. For example, target nucleic acid can be prepared as inserts of any of the conventional cloning vectors, including those used in conventional DNA sequencing. Extensive guidance for selecting and using appropriate cloning vectors is found in Sambrook et al., *Molecular Cloning: A Laboratory Manual*, Second Edition (Cold Spring Harbor Laboratory, New York, 1989), and like references. Sambrook et al. and Innis et al., editors, PCR Protocols (Academic Press, New York, 1990) also provide guidance for using polymerase chain reactions to prepare target polynucleotides. Cloned or PCR-amplified target nucleic acid is prepared which permit attachment to solid supports.

In a preferred embodiment, sheared DNA fragments from a subject organism, preferably human, are treated to provide blunt ends, then ligated to two oligodeoxynucleotides (ODNs). The first ODN is derivatized with biotin and the second is complementary to a sequencing primer. The ligated DNA is denatured, it is brought into contact with a streptavidin-activated slide, and it attaches through the biotin to the slide. A primer is hybridized to the tethered fragments prior to sequencing. Only DNA fragments having each type of ODN can both attach and be sequenced; fragments having two primer ODNs will not attach, and those having two attachment ODNs will not prime. DNA attachment could also be accomplished by direct covalent coupling as practiced on DNA chips (see, U.S. Pat. No. 5,605,662). Unlike DNA chips that require a dense lawn of probes, preferably, a few DNA molecules are bound per unit surface area. Binding density is easily controlled by adding a carrier to the DNA sample (e.g., free biotin to a biotinylated DNA sample).

The primers (DNA polymerase) or promoters (RNA polymerase) are synthetically made using conventional nucleic acid synthesis technology. The complementary strands of the probes are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, *Tetrahedron*, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the polymerase. They can be ordered commercially from a variety of companies, which specialize in custom oligonucleotides.

Purification of oligonucleotides, where necessary, is typically performed by either native acrylamide gel electrophoresis or by anion-exchange HPLC as described in Pearson and Regnier (1983) *J. Chrom.* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560.

While primers can hybridize to any of a number of sequences, selecting optimal primers is typically done using computer assisted consideration of available sequences and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length, G:C ratio, uniqueness in the given sequence, and the like.) based upon the known sequence. The selection of the hybridization properties of the primer is dependent on the desired hybridization and discrimination properties of the primer.

One of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767-5773 (1994); S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N.Y. provide a basic guide to nucleic acid hybridization. Innis supra provides an overview of primer selection.

Primers in combination with polymerases are used to sequence target DNA. Primer length is selected to provide for hybridization to complementary template DNA The primers will generally be at least 10 bp in length, usually at least between 15 and 30 bp in length. Primers are designed to hybridize to known internal sites on the subject target DNA. Alternatively, the primers can bind to synthetic oligonucleotide adaptors joined to the ends of target DNA by a ligase. Similarly where promoters are used, they can be internal to the target DNA or ligated as adaptors to the ends.

The reaction mixture for the sequencing comprises an aqueous buffer medium, which is optimized for the particular polymerase. In general, the buffer includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 microhms.

The divalent cation may be magnesium, manganese, zinc and the like, where the cation will typically be magnesium. Any convenient source of magnesium cation may be employed, including $MgCl_2$, Mg-acetate, and the like. The amount of Mg ion present in the buffer may range from 0.5 to 20 mM, but will preferably range from about 1 to 12 mM, more preferably from 2 to 10 mM and will ideally be about 5 mM.

Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.6 at 25° C. Other agents which may be present in the buffer medium include chelating agents, such as EDTA, EGTA and the like.

E. Detection

In certain embodiments, the enzymatic reaction is monitored using single molecule detection. The single-molecule fluorescence detection of the present invention can be practiced using optical setups including near-field microscopy, far-field confocal microscopy, wide-field epi-illumination, and total internal reflection fluorescence (TIRF) microscopy. Suitable photon detectors include, but are not limited to, photodiodes and intensified CCD cameras. In other embodiments, video chips such as CMOS chips can be used. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images in time (movies) of fluorophores. In certain aspects, each of the NTPs of the present invention has a unique fluorophore associated with it, as such, a four-color instrument can be used having four cameras and up to four excitation lasers or any combination thereof. Thus, it is possible to use this optical setup to sequence DNA. In addition, many different DNA molecules can be imaged and sequenced simultaneously. Moreover, with the use of image analysis algorithms, it is possible to track the path of single dyes and distinguish them from fixed background fluorescence.

In certain aspects, the preferred geometry for ICCD detection of single-molecules is total internal reflectance fluorescence (TIRF) microscopy. In TIRF, a laser beam totally reflects at a glass-water interface. The field does not end abruptly at the reflective interface, but its intensity falls off exponentially with distance. The thin "evanescent" optical field at the interface provides low background and enables the detection of single molecules with signal-to-noise ratios of about 6:1, preferably about 8:1 and more preferably about 12:1 at visible wavelengths (see, M. Tokunaga et al., *Biochem. and Biophys. Res. Comm.* 235, 47 (1997) and P. Ambrose, *Cytometry*, 36, 244 (1999)). In certain aspects, the TIR illumination field is continuously imaged at video-rate with an intensified charge couple device (ICCD) camera. It is thus possible to image the pyrophosphate as it is hydrolyzed by the enzyme.

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface, which corresponds to the contour length of about 600 base pairs of DNA. Either Prism-type or objective type TIRF geometry is for single-molecule imagining is used. (see, X-H. N. Xu et al., *Science*, 281, 1650 (1998) and Tokunaga et al., *Biochem Biophys. Research Comm.*, 235, 47 (1999)).

DNA, proteins and lipids have all been detected in complex samples with single-molecule sensitivity using labeled probes (see, L. Edman et al., *Proc. Natl. Acad. Sci. USA*, 93, 6710 (1996); M. Kinjo et al., *Nucleic Acids Res.* 23, 1795 (1995); A. Castro and J. G. K. Williams, *Anal. Chem.* 69, 3915 (1997); S, Nie, et al., *Science* 266, 1018 (1994); S, Nie, et al., *Anal. Chem.* 67, 2849 (1995); and T. Schmidt et al., *Proc. Natl. Acad. Sci. USA* 9, 2926 (1996)). In addition to simple detection, single fluorophores are also characterized with respect to fluorescence lifetime, spectral shifts and rotational orientation. In a preferred aspect of the present invention, an aqueous solution comprising an enzyme, such as a DNA polymerase, and distinguishable fluorogenic dNTPs, i.e., a characteristic dye for each nucleobase, flows across the surface. An evanescent light field is set up by total internal refection (TIR) of a laser beam at the glass-aqueous solution interface. In certain aspects, the TIR illumination field is continuously imaged at video-rate with an intensified charge couple device (ICCD) camera. It is thus possible to image the pyrophosphate as it is hydrolyzed by the enzyme.

Upon incorporation by polymerase, the dNTP is hydrolyzed as usual and the liberated terminal phosphate (e.g., pyrophosphate-dye) moiety diffuses into the surrounding medium. The free dye molecule, is imaged at video-rate under a microscope. A flowing stream sweeps the dye away from the parent DNA molecule. As the polymerase continues to move along the DNA, the nucleotide sequence is read from the order of released dyes. Sequencing proceeds quickly, as fast as the polymerase progresses along the DNA template.

In another embodiment, the present invention includes sensors as disclosed in U.S. Pat. No. 5,814,524, which issued to Walt et al., on Sep. 29, 1998. An optical detection and identification system is disclosed therein that includes an optic sensor, an optic sensing apparatus and methodology for detecting and evaluating one or more analytes or ligands of interest, either alone or in mixtures. The system is comprised of a supporting member and an array formed of heterogeneous, semi-selective polymer films which function as sensing receptor units and are able to detect a variety of different analytes and ligands using spectral recognition patterns. Using this system, it is possible to combine viewing and hemical sensing with imaging fiber chemical sensors.

In yet another embodiment, the detection is accomplished using blockade current, as described in U.S. Pat. No. 5,795,782 issued to Church et al., and which is incorporated herein by reference in its entirety for all purposes. As disclosed therein, two pools of medium used may be any fluid that permits adequate analyte mobility for interface interaction. Typically, the pools will be liquids, usually aqueous solutions or other liquids or solutions in which the analyte can be distributed. The interface between the pools is designed to interact sequentially with the analyte molecule one at a time. The useful portion of the interface may be a passage in or through an otherwise impermeable barrier, or it may be an interface between immiscible liquids. It is preferable that only one passage is present or functional in the impermeable barrier. The interface-dependent measurements can be any measurement, e.g., physical or electrical, that varies with analyte-interface interaction. For example, physical changes the analyte cause as they interact sequentially with the interface may be measured. Current changes resulting from the analyte's interference with ion flow at the interface may be measured. The measurements may reflect the sequential interaction of the analyte with the interface, so as to permit evaluation of sequence-dependent characteristics.

In one embodiment, the pools include electrically conductive medium, which can be of the same or different compositions. The pools with conducting media are separated by an impermeable barrier containing an ion-permeable passage, and measurements of the interface characteristics include establishing an electrical potential between the two pools such that ionic current can flow across the ion permeable passage. When the analyte interacts sequentially with the interface at the ion permeable passage, the ionic conductance of the passage will change (e.g., decrease or increase) as each analyte interacts.

The conducting medium used can be any medium, preferably a solution, more preferably an aqueous solution, which is able to carry electrical current. Such solutions generally contain ions as the current conducting agents, e.g., sodium, potassium, chloride, calcium, cesium, barium, sulfate, and phosphate. Conductance (g) across the pore or channel is determined by measuring the flow of current across the pore or channel via the conducting medium. A voltage difference can be imposed across the barrier between the pools by conventional means, e.g., via a voltage source, which injects or administers current to at least one of the pools to establish a potential difference. Alternatively, an electrochemical gradient may be established by a difference in the ionic composition of the two pools, either with different ions in each pool, or different concentrations of at least one of the ions in the solutions or media of the pools. In this embodiment of the invention, conductance changes are measured and are indicative of analyte-dependent characteristics.

F. High Throughput Screening The present invention also provides integrated systems for high-throughput screening of DNA sequencing and pyrophosphate detection. The systems typically include robotic armature, which transfers fluid from a source to a destination, a controller that controls the robotic armature, an ICCD camera, a data storage unit which records the detection, and an assay component such as a microtiter dish or a substrate comprising a fixed reactant. A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to set up several parallel simultaneous polymerase reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image. In certain aspects, the integrated system of the present invention carries light from the specimen field to the charge-coupled device (CCD) camera, which includes an array of picture elements (pixels). The light from the specimen is imaged on the CCD camera. Particular pixels corresponding to regions of the specimen (e.g., individual polymerase sites on a glass surface) are sampled to obtain light intensity readings for each position. Multiple pixels are processed in parallel to increase speed. The apparatus and methods of the invention are easily used for viewing any sample, e.g., by fluorescent or dark field microscopic techniques.

IV. Systems

Figure 9:
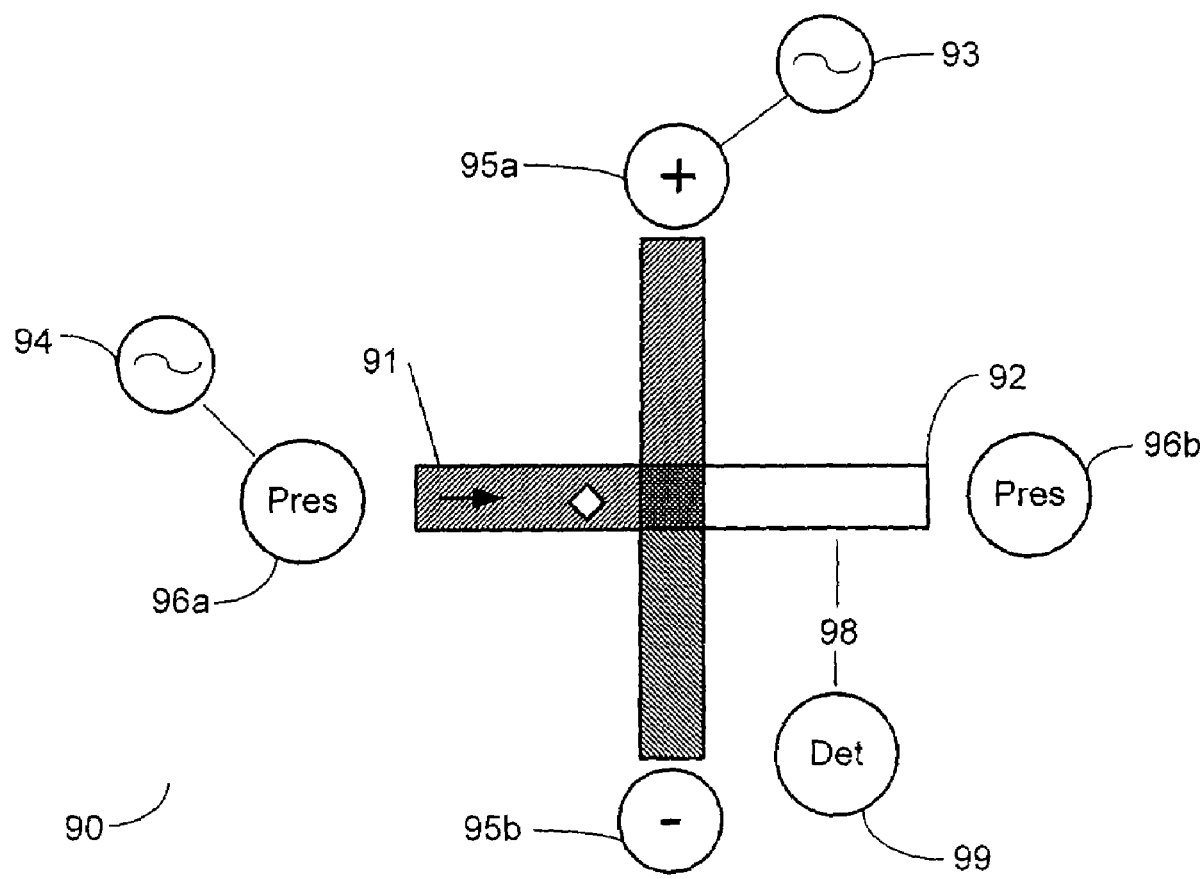
FIG. 9 illustrates a schematic of an embodiment of microfabricated flowcell of the present invention.

FIG. 9 is a schematic of a microfabricated flowcell system 90 of the present invention. This diagram is merely an illustration and should not limit the scope of the claims herein. One of ordinary skill in the art will recognize other variations, modifications, and alternatives.

As shown therein, the present invention provides a microfabricated flowcell 90 having an inlet port 91 and an outlet port 92 wherein a sample stream having a detectable analyte flows therethrough. In certain aspects, the system includes at least a first energy field source 93 having an energy field transverse to the sample stream. In some embodiments, the system comprises a second energy field source 94 having a second energy field axial to the sample stream. The transverse field has a pair of electrodes 95a, 95b and optionally, the axial field has a hydrostatic pressure differential 96a, 96b. The system also includes a detector 99 for detecting the analyte in a microchannel zone 98. Suitable energy fields include, but are not limited to, an electric field, a thermal field, a magnetic field, an electromagnetic field, a photoelectric field, a light field, a mechanical field, a pressure field or combinations thereof. Preferably electric and pressure fields are employed.

In certain embodiments, the flowcell is fabricated by microfabrication methods known to those of skill in the art. For example, precision injection molded plastics or molded elastomers can also be used for fabrication. The flowchamber can be made of plastic or glass and should either be open or transparent in the plane viewed by the detector, microscope or optical reader.

In one embodiment, the flowcell is about 0.1 mm to about 100 cm in length, preferably about 1 mm to about 10 cm in length. In certain aspects, the flowcell has channels for the sample stream that can be of different dimensions and are typically about 0.5-10 cm in length and have a depth of 0.5-100 μm. Channel dimensions can vary from place to place within the same flowcell. The shape of the channel can vary and can be rectangular, oval, circular, triangular, trapezoidal or otherwise. In certain aspects, various channel shapes are present. The width of the channel is typically about 1 μm to about 100 μm.

In certain embodiments, the system may also include an analyte stream introduced into the inlet port 91 comprising a liquid carrier containing substrate particles, nucleotides, enzymes, and the like. In certain embodiments, the analyte is immobilized on a solid support such as a bead, and the bead may be trapped on a feature in the microchannel. The liquid carrier can be any fluid capable of accepting particles from a feed stream and containing an indicator substance. Preferred sample streams comprise water and solutions such as salt water with buffered solution well known to those of skill in the art. Alternatively, various organic solvents are suitable such as acetone, isopropyl alcohol, ethanol, or any other liquid convenient that does not interfere with detection.

As disclosed in PCT publication No. WO 00/36152 and incorporated herein by reference, in a preferred embodiment, each nucleotide has a unique fluorophore associated with it, as such, a four-color instrument can be used having four cameras and four excitation lasers, or one camera with an image splitter device, or less than four excitation lasers as sufficient to excite the four different dyes. Thus, it is possible to use this optical setup to sequence DNA. In addition, many different DNA molecules immobilized in microchannels can be imaged and sequenced simultaneously. Moreover, with the use of image analysis algorithms, it is possible to track the path of single dyes and distinguish them from fixed background fluorescence.

In an alternative embodiment, the nucleotides disclosed in U.S. Pat. No. 6,232,075, issued Mar. 15, 2001 to Williams, and which is incorporated herein by reference in its entirety for all purposes, can be used. As disclosed therein, nucleotide probes having fluorescent labeled attached thereto are disclosed.

In certain other embodiments, detection and analysis is done by various methods known to the art, including optical means, such as optical spectroscopy, and other means such as absorption spectroscopy, Raman spectroscopy or fluorescence, by chemical indicators which change color or other properties when exposed to the analyte, by immunological means, electrical means, e.g., electrodes inserted into the device, electrochemical means, blockade current means, radioactive means, or virtually any microanalytical technique known to the art to detect the presence of an analyte such as an ion, molecule, polymer, virus, nucleic acid sequence, antigen, microorganism, and the like. Preferably optical or fluorescent means are used, and antibodies, nucleotides and the like are attached to fluorescent markers.

In certain other embodiments, the flowcell system of the present invention further optionally comprises voltage probes, conductivity electrodes, pH cells, conductivity meters, pH meters, ammeters, voltmeters, flowrate monitors, a data acquisition system and a microcomputer. Those of skill in the art will recognize useful additional sensors and probes.

Figure 10:
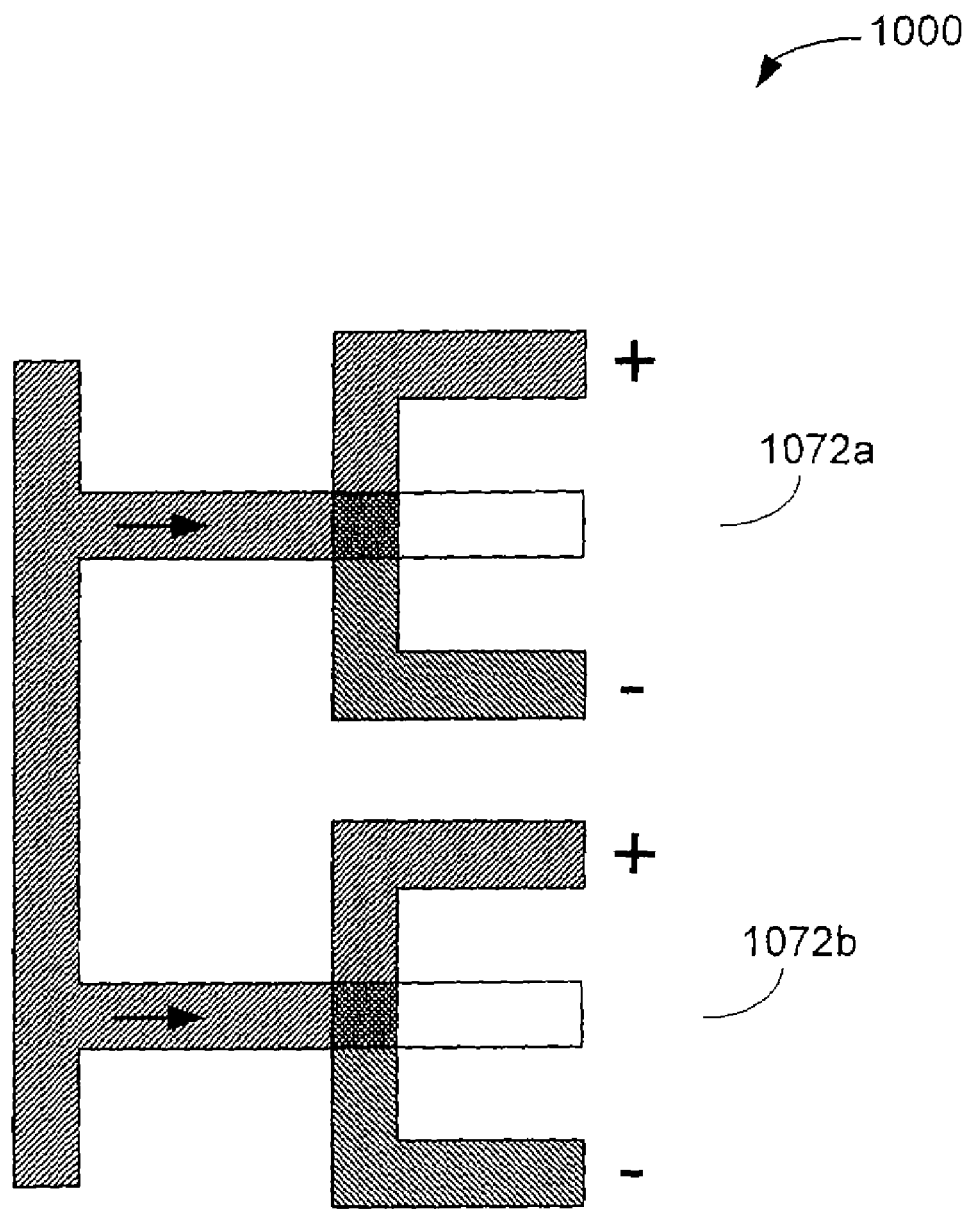
FIG. 10 illustrates a schematic of an embodiment of microfabricated flowcell of the present invention.

FIG. 10 is a schematic of a microfabricated flowcell system of the present invention having a plurality of flowcells (an array of flowcells). This diagram is merely an illustration and should not limit the scope of the claims herein. One of ordinary skill in the art will recognize other variations, modifications, and alternatives.

In this embodiment, the flowcell system 1000 of the present invention is extended into an array of flowcells 1072a, 1072b with a plurality of components. As used herein array is at least two flowcells. For instance, it is possible to have multiple immobilization sites, inlet and outlet ports, detectors and the like.

V. EXAMPLES

The following examples are offered to illustrate, but not to limit the claimed invention.

Example I

This example shows an algorithm for calculating charge on the intact nucleotide probe and cleavage product, taking into account contributions from hydrogen ions and divalent metal cations. It will be appreciated by those of skill in the art that particular equilibrium constants are affected by the instant chemical environment, and that the equilibrium constants affect the outcome of the calculation. The algorithm explained in the example was implemented in a computer program to execute the calculations, some results of which are illustrated in FIG. 3.

For steps 1-3 below, refer to FIG. 5 for the definition of the indicated equilibrium constants K (in boxes). Values for the equilibrium constants are taken from analogous compounds in Frey and Stuhr (1972) *Journal of the American Chemical Society*, 94:8898. In the calculation steps, these definitions apply: N-PPP-F "L" (ligand); H$^+$="H" (hydrogen ion) and Mg$^{++}$="M" (counter ion metal).

I. Step 1 $K_{HL}$

Compute H Binding to L at a Given pH:

The Equilibrium $$L+H \leftrightarrow LH$$

$$K_{HL}=[LH]/[L]*[H]$$

Value of $K_{HL}$

LOG $K_{HL} \cong 2$ the primary ionization of all nucleotide mono, di and triphosphates f1, the Fraction of L in Protonated Form LH $$f1=[H]/([H]+K_{HL})$$

$$f1 \cong 0$$

f2, the Fraction of L in Unprotonated Form L $$f2=1-f1$$

$$f2 \cong 1 \text{ at neutral pH}$$

II. Step 2-$K_{ML}$

Compute M Binding to L at a Given [M] at the of Step 1

The Equilibrium $$L+M \leftrightarrow LM$$

$$K_{ML}=[LM]/[L]*[M]$$

Value of $K_{ML}$ $$\log K_{ML}=2.18$$

the analog of N-PPP-F is protonated-NTP (NTP-H), where H≅F $$\text{ATP-H}+Mg \leftrightarrow \text{ATP(Mg)-H}, \log K=2.18$$

$$\text{CTP-H}+Mg \leftrightarrow \text{CTP(Mg)-H}, \log K=2.18$$

f5, the Fraction of L in Complexed Form ML $$f5=[M]/([M]+K_{ML})$$

f6, the Fraction of L in Uncomplexed Form L $$f6=1-f5$$

III. Step 3 $K_{MHL}$

Compute M Binding to HL at a Given [M] at the PH of Step 1

The Equilibrium $$HL+M \leftrightarrow MHL$$

$$K_{MHL}=[MHL]/[HL]*[M]$$

Value of KMHL

[HL] is negligible

[HL] is negligible because at neutral pH values, L is in the unprotonated form ($K_{HL}\cong 2$; above)

IV. Step 4

Compute the Fraction of Each Complexed Form of L (Refer to FIG. 5)

$$\text{frac}L=f2*f6$$

$$\text{frac}ML=f2*f5$$

$$\text{frac}HL=f1*f4 \cong 0*f4 \cong 0$$

$$\text{frac}MHL=f1*f3 \cong 0*f3 \cong 0$$

V. Step 5

Compute Phosphate Charge $Q_{phos}$ Averaged Over all Forms of L $$Q_{phos}=Q(L)*\text{frac}L+Q(ML)*\text{frac}ML+Q(HL)*\text{frac}HL+Q(MHL)*\text{frac}MHL$$

where each Q is defined in the FIG. 5

VI. Step 6

Compute Nucleobase Charge $Q_B$ Due to Nucleobase Adducts B

The Equilibrium $$B+H \leftrightarrow BH$$

$$KBH=[BH]/[B]*[H]$$

value of $K_{BH}$ depends on whether the adduct B is for example a carboxylate (−) or arginine(+) or quaternary amine(+)

$\log K_{BH}$=4.5 for carboxylate $\log K_{BH}$=12 for arginine or quaternary ammonium salt note: at pH values 6.5-8.5, these groups are effectively fixed negative or positive charges Fraction of Protonated and Unprotonated Forms $$\text{frac}BH=[H]/([H]+K_{BH})$$

$$\text{frac}B=1-\text{frac}BH$$

Charge $Q_B$=charge of B $Q_{BH}$=charge of BH $$Q_B=\text{frac}BH*Q_{BH}+\text{frac}B*Q_B$$

VII. Step 7

Compute γ-Label Charge $Q_G$ from γ-Label Adducts G same logic as step 6

$$Q_G=\text{frac}GH*Q_{GH}+\text{frac}G*Q_G$$

VIII. Step 8

Compute Overall Charge $Q_{N-PPP-F}$ on N-PPP-F $$Q_{N-PPP-F}=Q_{phos}+Q_B+Q_G$$

Similar to the above, equilibrium calculations can be done for PP-F. The same logic applies as for N-PPP-F, except that different equilibrium constants are used which are appropriate for PP-F (values given in boxes below). For steps 1-3 below, refer to FIG. 5 for the definition of the indicated equilibrium constants K (in boxes). Values for the equilibrium constants are taken from analogous compounds in Frey and Stuhr (1972) JACS 94:8898. The following definitions apply PP-F="L" (ligand); H$^+$="H" (hydrogen ion) and Mg$^{++}$="M" counter ion or (metal).

I. Step 1-$K_{HL}$

Compute H Binding to L at a Given pH:

The Equilibrium $$L+H \leftrightarrow LH$$

$$K_{HL}=[LH]/[L]*[H]$$

VALUE OF $K_{HL}$ $\log K_{HL}\cong 2$ the primary ionization of all nucleotide mono, di and triphosphates f1, the Fraction of L in Protonated Form LH $$f1=[H]/([H]+K_{HL})$$

$f1 \cong 0$ at neutral pH f2, the Fraction of L in Unprotonated Form L $$f2=1-f1$$

$f2 \cong 1$ at neutral pH

II. Step 2-$K_{ML}$

Compute M Binding to L at a Given [M] at the pH of Step 1

The Equilibrium

L+M⇌LM $K_{ML}=[LM]/[L]*[M]$

Value of $K_{ML}$ log $K_{ML}$=3.20 the analog of PP-F is unprotonated nucleotide diphosphate or protonated pyrophosphate ADP+Mg⇌ADP(Mg), log K=3.22

DP+Mg⇌CDP(Mg), log K=3.21

PP-H+Mg⇌(Mg)PP-H, log K=3.18 f5, the Fraction of L in Complexed Form ML $f5=[M]/([M]+K_{ML})$ f6, the Fraction of L in Uncomplexed Form L $f6=1-f5$ III. Step 3-$K_{MHL}$ Compute M Biding to HL at a Given [M] at the pH of Step 1

The Equilibrium

HL+M⇌$K_{MHL}$ $K_{MHL}=[MHL]/[HL]*[M]$

Value of $K_{MHL}$ log $K_{MHL}$=1.60 the analog of H-PP-F is protonated nucleotide diphosphate N-PP-H

ADP(H)+Mg⇌ADP(H)-Mg, log K=1.55

CDP(H)+Mg⇌ADP(H)-Mg, log K=1.60 f3, The Fraction of HL in Complexed Form MHL $f3=[M]/([M]+K_{MHL})$ f4, The Fraction of HL in Uncomplexed Form HL $f4=1-f3$ IV. Step 4

Compute the Fraction of Each Complexed Form of L (Refer to Figure)

$fRacL=f2*f6$ $fracML=f2*f5$ $fracHL=f1*f4$ $fracMHL=f1*f3$

V. Step 5

Compute Phosphate Charge $Q_{phos}$ Averaged Over all Forms of L $Q_{phos}=Q(L)*fracL+Q(ML)*fracML+Q(HL)*fracHL+Q(MHL)*fracMHL$ where each Q is defined in the Figure VI. Step 6

Compute Nucleobase Charge $Q_B$ Due to Nucleobase Adducts B

The Equilibrium

B+H⇌BH $KBH=[BH]/[B]*[H]$ value of $K_{BH}$ log $K_{BH}$=4.5 for carboxylate log $K_{BH}$=12 for arginine or quaternary ammonium salt note: at pH values 6.5-8.5, these groups are effectively fixed negative or positive charges Fraction of Protonated and Unprotonated Forms $fracBH=[H]/([H]+K_{BH})$ $fracB=1-fracBH$ Charge $Q_B$=charge of B $Q_{BH}$=charge of BH $Q_B=fracBH*Q_{BH}+fracB*Q_B$ VII. Step 7

Compute γ-Label Charge $Q_G$ from γ-Label Adducts G same logic as step 6

$Q_G=fracGH*Q_{GH}+fracG*Q_G$

VIII. Step 8

Compute Overall Charge $Q_{N-PPP-F}$ on N-PPP-F $Q_{N-PPP-F}=Q_{phos}+Q_B+Q_G$

Example II

Materials and Methods

Modeling was performed of nucleotide sequencing using the system of the present invention. The simulations were performed with MATLAB (The MathWorks, Inc., Natick, Mass.) version R11.1, running on an Intel Pentium III-based machine. The operating system is Windows 98 (second edition). Nucleotide motion was calculated according to the following method. For each time step, 1. Determine the voltage at this time for both pairs of plates from a given waveform.
2. Calculate the electric field in the axial and transverse directions due to the voltage. Add in a vector-wise fashion for the total field.
3. Calculate the resultant velocity given the physical parameters of the molecule. Note that the charge and diffusion coefficient will be different for the quencher-nucleobase-dye moiety than for the released pyrophosphate-dye moiety.
4. Given the time step, calculate the resultant motion from the velocity.
5. Calculate a Gaussian-distributed movement due to diffusion.
6. Add the movement due to diffusion and the movement due to the electric field in a vector-wise fashion.
7. Move the molecule.

A. This example is similar to an electrophoretic case, wherein a DC field is applied axially.

In this example, no field is applied to the transverse plates, and a constant field is applied to the axial plates. The charge on the dye-nucleobase-quencher structure is −4, and the charge on the pyrophosphate-dye structure is −2. The axial field strength is $3 \times 10^5$ V/m, which would result from, for example, 3000 V across 1 cm.

In this example, the charge ratio between the unincorporated structures and the released dyes is 2, meaning that on average, the unincorporated structures travel twice as fast as the released dyes.

B. This example illustrates a DC field applied axially and an AC field applied transversely.

In this example, the transverse field is modulated in a sinusoidal fashion. The charge ratio is 2. The axial field strength is the same as in Example 1, and the transverse field has a peak-to-peak amplitude of 50 V. The frequency of oscillation is 200 Hz. The background molecules spread or "throw" their photons over a larger area, since their spatial modulation (peak-to-peak length of their paths) is greater due to stronger response to the E field. This has the effect of smoothing out the background, resulting in a higher signal-to-noise ratio (SNR). The preferred setup is to have the released phosphate have a small, but distinguishable path amplitude (if the amplitude were too great, it would also scatter its photons over too many CCD pixels).

Example III

This example illustrates an AC field applied axially and an AC field applied transversely.

Another case of interest is to have only AC components to the transverse and axial fields. If both field strengths are sinusoids comparable in amplitude and frequency, the resultant path coupled with diffusion paints a bright spot on the image when an incorporation event occurs. This method allows a continual "wash" over the enzymes to encourage incorporation, while limiting the total traversal breadth to keep photons concentrated in one place. Moreover, it is advantageous to use this method when the CCD camera is reading out and the shutter is closed, to avoid having signals travel far away during the "blackout" time (images are not being recorded). The peak axial field strength is the same as the previous two DC examples, while the peak transverse voltage is 50 V. Both waveforms are at 200 Hz.

Example IV

This example illustrates an AC and DC field applied axially and an AC applied transversely.

Applying both AC and DC fields to the axial plates results in shorter, fatter streaks since the molecules follow a spiral pattern down the flowcell. The DC component ensures eventual washing away of all molecules. The AC field in the transverse direction encourages unincorporated molecules to throw their photons over a larger area, which as before tends to smooth out the background.

Example V

This example illustrates that $Mg^{++}$ can change the electrophoretic mobility of dTTP and dTDP (unlabeled) from more negative to less negative. It also shows that the electrophoretic mobility of dTTP-(++)-BODIPYTR can be changed from negative to positive as the $Mg^{++}$ concentration increases.

5.1 Analysis of dTTP and dTDP by Capillary Electrophoresis

Figure 11:
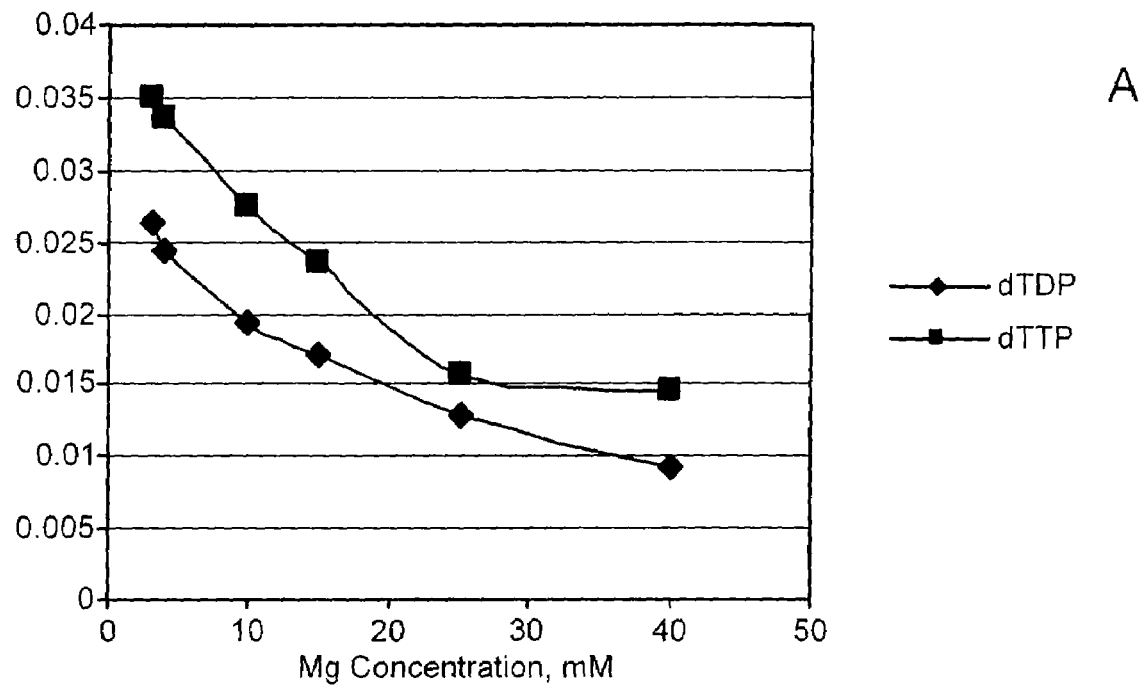
FIG. 11 PANEL A nucleotide electrophoretic velocities are plotted as a function of $Mg^{++}$ concentration. Panel B effect of $Mg^{++}$ on electrophoretic migration of the compound in FIG. 4 in agarose gels containing the indicated amounts of $Mg^{++}$.
Figure 11:
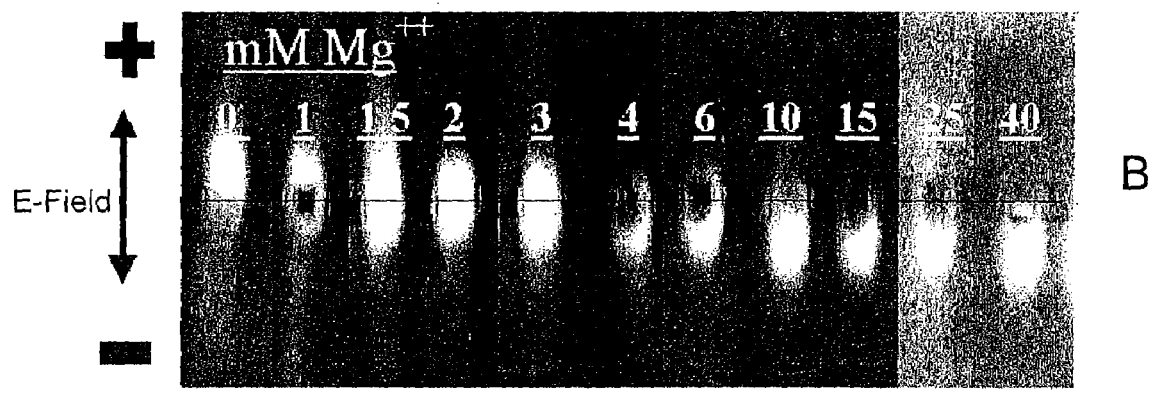

The effect of $Mg^{++}$ on the electrophoretic mobility of dTTP and dTDP was determined by capillary electrophoresis. Electrophoresis buffer contained 50 mM Tris-acetate pH 8.0, 60 mM KCl, and various concentrations of $MgCl_2$ (3, 4, 6, 10, 15, 25 and 40 mM). The sample contained 0.5 mM nucleotide (dTTP or dTDP; Sigma) and 0.8 mM mesityl oxide (electroneutral marker; Sigma). The samples were analyzed by capillary electrophoresis (Hewlett Packard) using an uncoated fused silica capillary (40 cm from injection end to detection zone). Voltage was 8.5 kV and peaks were monitored by optical absorbance at 260 nm. Electrokinetic velocity of each sample peak was calculated by dividing distance (40 cm) by elution time. Electroosmotic flow (EOF) of the bulk buffer is taken as the velocity of the mesityl oxide marker. Nucleotide electrophoretic velocity is the nucleotide electrokinetic velocity minus EOF. Nucleotide electrophoretic velocities are plotted as a function of $Mg^{++}$ concentration (FIG. 11A). The dTTP has a more negative electrophoretic mobility than the dTDP, as expected, because dTTP has an additional phosphate group ("negative mobility" means that the molecule moves like a negatively-charged molecule, towards the positive electrode). $Mg^{++}$ changed the electrophoretic mobility of both nucleotides from more negative to less negative.

5.2 Analysis of dTTP-BQS(++)-BODIPYTR by Gel Electrophoresis

The net charge on dTTP was adjusted in a positive direction by adding two quaternary amine groups on a linker attached to the γ-phosphate; an electroneutral dye marker was also attached to the linker, giving the compound dTTP-BQS(++)-BODIPYTR (FIG. 4). The effect of $Mg^{++}$ on the electrophoretic mobility of this nucleotide was determined by agarose gel electrophoresis. Electrophoresis buffer contained 50 mM Tris-acetate pH 8.0, 60 mM KCl, and various concentrations of $MgCl_2$ (0, 1, 1.5, 2, 3, 4, 6, 10, 15, 25 and 40 mM). Slab gels (4% agarose) were cast in each electrophoresis buffer and each gel was placed in a slab gel apparatus (Bio-Rad) containing the respective electrophoresis buffer. The sample wells were loaded with 5 µL of 20 µM dTTP-BQS (++)-BODIPYTR and electrophoresis was performed at 6 V per cm for 10 min. The gels were photographed on a UV transilluminator and the separate images were assembled into a single FIGURE (FIG. 11B). As was seen with unlabeled dTTP (FIG. 11A), $Mg^{++}$ added positive charge to the nucleotide. However, because the two quaternary amines make the labeled nucleotide less negative as compared to the unlabeled nucleotide, the effect of $Mg^{++}$ is to change the nucleotide mobility from net negative to net positive.

Example VI

This example illustrates the synthesis of a charge-switch nucleotide of the present invention.

6.1 Preparation of Compound 1'

Figure 12:
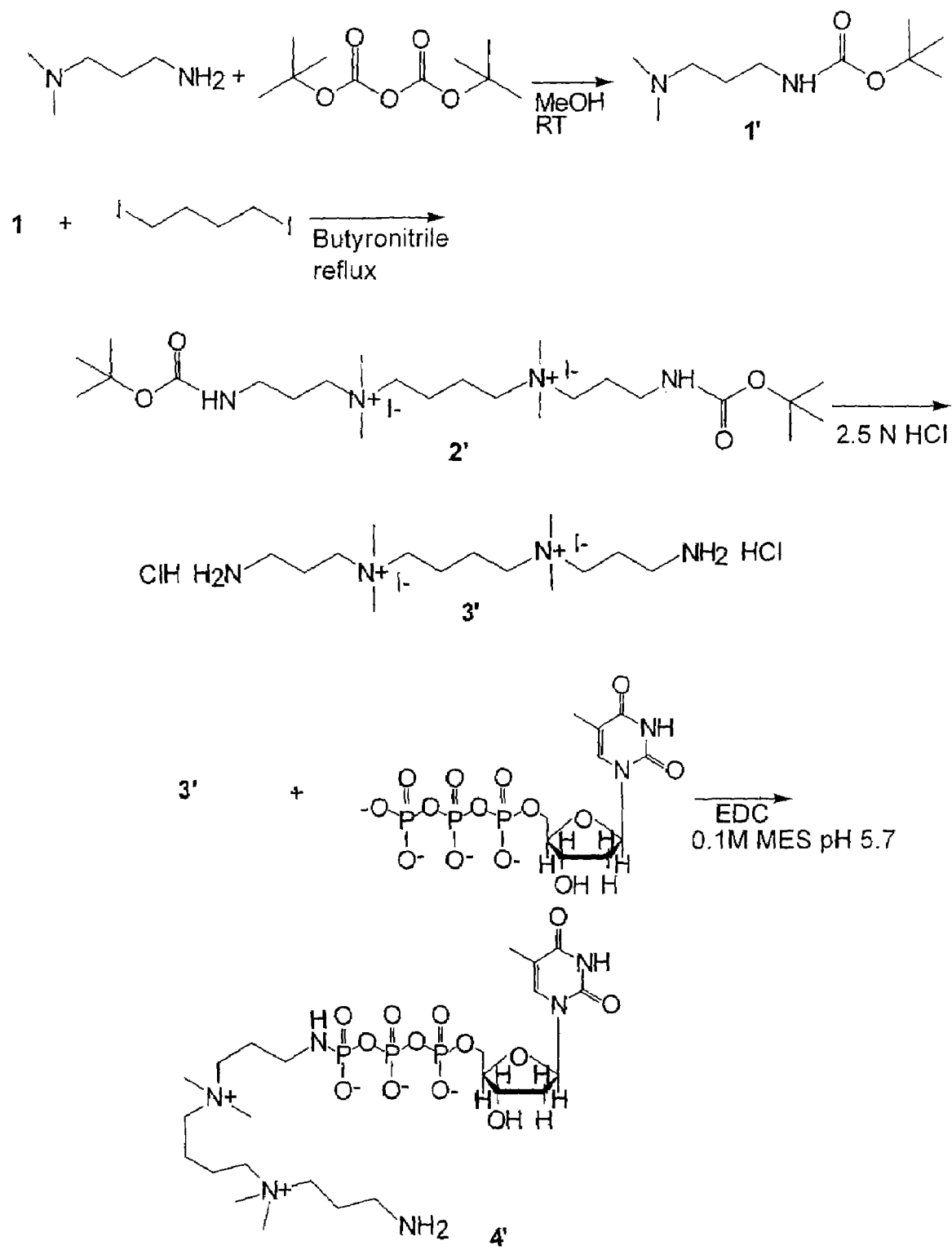
FIG. 12 illustrates a synthetic scheme of an embodiment of the present invention.
Figure 12:
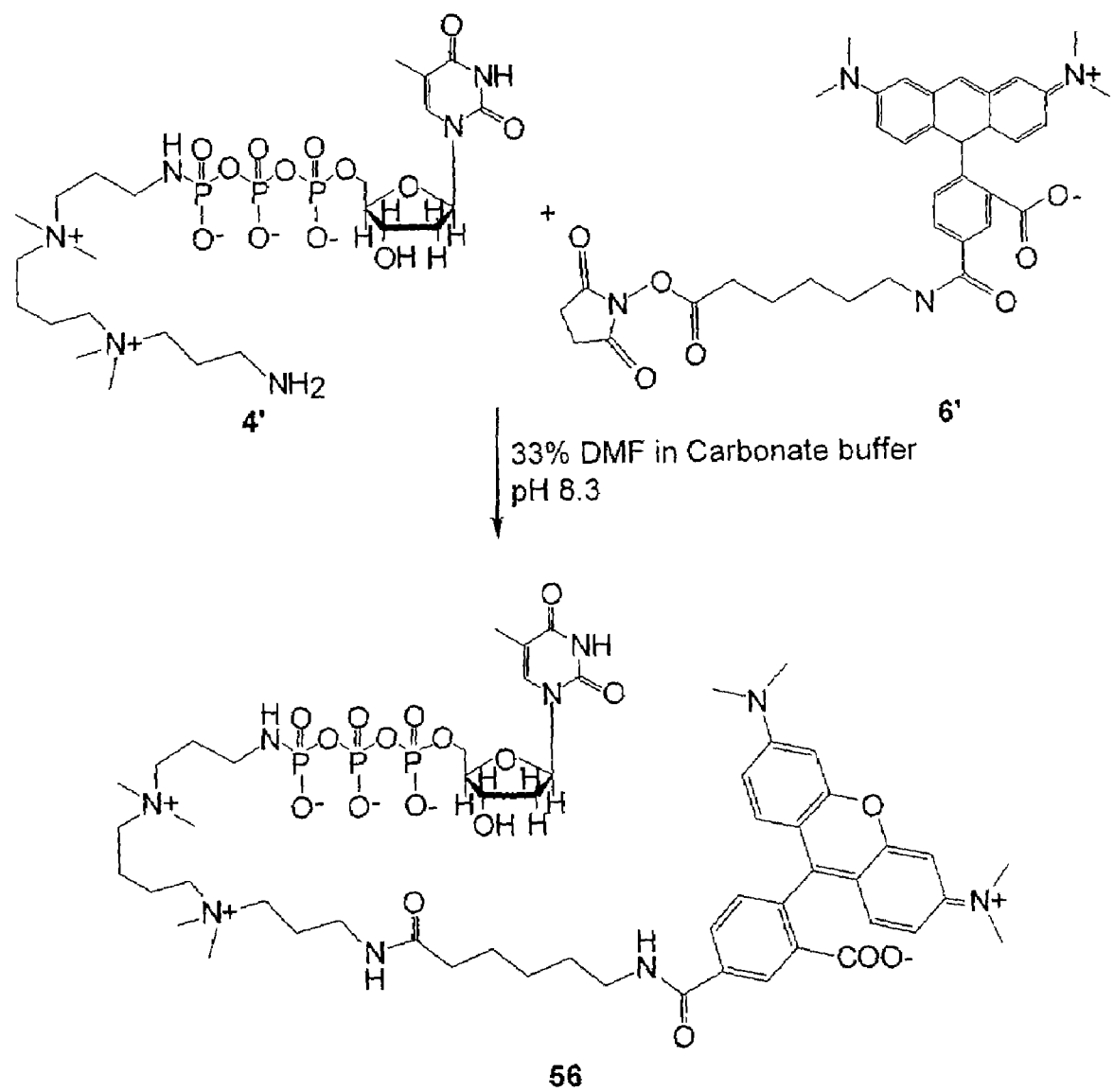

In FIGS. 12A and B, 11.2 g of t-BOC anhydride (Aldrich, 218 g/mol, 52.4 mmole) is dissolved in 100 mL of reagent grade methanol (Fisher). 10 mL of N,N dimethylpropyl amine (Aldrich, 102.1 g/mol, 48.9 mmole) is added slowly to the reaction mixture. The reaction mixture is allowed to stir at room temperature for 16 hours. The reaction is deemed complete by TLC (C18, 1:1 Acetonitrile/Methanol, $I_2$ visualization) Solvent is evaporated in vacuo. Compound 1' (FIG. 15) is then purified by column:chromatography (1:1 methylene chloride and methanol). Fractions containing pure compound 1 were combined and evaporated in vacuo to yield 17.7 g of purified product.

6.2 Preparation of Compound 2'

2.16 g of compound 1 (202 g/mol, 10.7 mmole) is dissolved in 10 mL dry reagent grade butyronitrile (Fisher). 1.51 grams of 1,4-diiodobutane is added and the mixture is refluxed at 135° C. for 24 hours. The reaction is checked by TLC (C18, 40% aqueous methanol, $I_2$ visualization) and determined to be complete. The reaction mixture is precipitated with diethyl ether and collected. After dissolving in methanol, the product is again precipitated with diethyl ether. The resultant viscous yellow residue is dissolved in methanol and the solvent is removed in vacuo. This material is used without purification to form compound 3.

6.3 Preparation of Compound 3'

After drying, compound presents as fluffy yellow solid. This material is dissolved in 20 mL of 5N HCl (prepared from concentrated HCl, Fisher) and stirred at room temperature for 5 hrs. Reaction completion is checked by TLC (C18, 1:1 Acetonitrile/methanol, ninhydrin and UV visualization). The acid solution is concentrated and product of interest is precipitated with diethyl ether. This solid is redissolved in methanol and re-precipitated in diethyl ether. The solid is collected and dried under vacuum. This product is used without further purification or determination of yield.

6.4 Preparation of Compound 4'

1.1 mg of dTTP (Sigma, 492.7 g/mol, 2.2 μmole) is dissolved in 100 μL 0.1 M MES pH 5.7. In a separate vial, 19.7 mg of EDC (Aldrich, 191.7 g/mol, 100 μmole) is dissolved in 100 μL of 0.1 M MES pH 5.7. These two solutions are combined and allowed to incubate at room temperature for 10 minutes.

11.6 mg of compound 3 is dissolved in 400 μl of MES buffer. The pH of this solution is checked with pH strips and found to be 5.8. This solution is added to the activated nucleotide and the reaction is allowed to stand at room temperature for 110 minutes. The reaction is monitored by reverse phase HPLC. The product of interest is isolated by reverse phase HPLC (C18, 4-80% Acetonitrile in 0.1 M TEAA over 20 minutes). Solvent is removed from purified compound #4 in vacuo. Yield is 12.7% from dTTP.

6.5 Preparation of Compound 56

Compound 4' (0.15 μmole, 975 g/mol) is dissolved in 100 μl of 50 mM carbonate buffer at pH 8.3. pH is checked by colorpHast pH strips and found to be 8.3. 9.4 μL of 22 mM TAMRA-X-SE 6' (Molecular Probes, 640.59 g/mol, 0.23 μmole) is added and the reaction mixture is allowed to stand at room temperature for 18 hours in the dark. Reaction is determined complete after hydrolysis of all active dye ester. Product of interest 56 is isolated by reverse phase HPLC (C18, 4-80% Acetonitrile in 0.1 M TEAA over 20 minutes). Solvent is removed from product in vacuo in the dark. Yield is 30% from compound 4.

Example VII

This example illustrates an assay system to demonstrate charge-switching activity of compounds of the present invention.

This assay is used to test for a change in the electric charge associated with a dye attached to the phosphate of a nucleotide. The charge switch on the dye is caused by cleavage of a phosphodiester bond that links the dye to the nucleotide. In this example, cleavage is catalyzed by snake venom phosphodiesterase.

Phosphodiesterase I (from Crotalus adamanteus venum; USB Corp.) was dissolved in 110 mM Tris-HCl (pH 8.9) containing 110 mM NaCl, 15mM $MgCl_2$, to a final enzyme concentration of 40 units/mL. The reaction sample (50 μL) contained Phosphodiesterase I (3.6 units/mL), HEPES-NaOH buffer (40 mM) and dTTP-BQS-BTR (38 μM). A control sample was the same as the reaction sample except that the enzyme was omitted. The reaction and control samples were incubated at 37° C. for 1 hour and were analyzed by electrophoresis in a 5% agarose using a running buffer comprising 50 mM Tris-HCl pH 8.0, 60 mM KCl, 2 mM $MgCl_2$. The BTR dye in the reaction sample migrated toward the negative electrode (−), while the dye in the control sample migrated toward the positive electrode (+).

Example VIII

This example demonstrates charge-switching activity of compounds of the present invention.

Materials

Microchannels were created by replica molding polydimethylsiloxane (PDMS) against a silicon master. The channels are 10 microns wide by 10 microns deep. Two intersecting channels perpendicular to one another were formed in the shape of a cross. The distal ends of each channel empty into separate circular wells of diameter 4 mm and depth 5 mm.

With reference to FIG. 9, platinum electrodes were placed into the wells of the vertical channel 95a, 95b. (Although not explicitly shown in the FIG. 9, the distal ends of each channel empty into separate circular wells i.e., 95a, 95b; and 96a, 96b. For this embodiment, the designations 95a, 95b and 96a, 96b are used interchangeably to denote the wells of the channels and the electrodes and pressure forces respectively). Voltage was applied across these electrodes to introduce an electric field down the vertical channel. Simultaneously, pressure was applied to both wells 96a, 96b. Pressure applied to well 96a forces dye towards the cross intersection, while pressure applied to well 96b prevents dye from continuing towards well 96b (dye is forced into the vertical channel towards either well 95a, 95b.

The 530.9 line of a tunable argon-krypton laser was used to directly illuminate the flowcell channels. A cleanup filter (center wavelength 530 nm, bandwidth 10 nm) was inserted between the laser output and the flowcell. The emitted fluorescence was viewed with an inverted microscope using an air objective (10×, NA 0.25). After the objective a holographic notch filter (center wavelength 530.9 nm, bandwidth 3 nm) and a bandpass emission filter (center wavelength 575 nm, bandwidth 50 nm) removed Rayleigh and Raman scatter. The resulting signal was imaged onto a CCD camera and captured onto a PC with frame grabber hardware and software.

The buffer consisted of a mixture of 20 mM Tris-OAc pH 8, 3% (w/v) polyvinylpyrolidone (PVP), 2 mM $MgCl_2$, and 0.1% Tween 20. A buffer+dye solution was formed by adding either gly-TAMRA (−1 charge) or BQS-TAMRA (+1 charge) dye to the same buffer constituents, such that the dye concentration was 1 μM.

The PDMS molds and borosilicate cover slips were treated in an oxygen plasma chamber for 1 minute. After treatment, upon contact the PDMS and glass would irreversibly bond. The plasma also causes the flowcell and glass surfaces to become hydrophilic, permitting easy filling of the channels by capillary action.

I. The purpose of this experiment was to show that the negatively charged dye could be forced to turn a corner by the application of an electric field while suppressing electroosmotic flow (EOF).

Wells at the end of the vertical channels 95a, 95b, and at the end of the horizontal channel 96b were filled with 40 μL of buffer solution while watching the cross intersection on a monitor showing the magnified image. After the channels were wetted, well 96a was filled with 40 μL of buffer+dye solution. A pressure of 0.28 psi was applied to well 96a, while simultaneously applying 0.43 psi to well 96b. An electric field of 820 V/cm was applied from well 95a to well 95b (well 95a containing the positive electrode).

The electric field forces the negatively-charged dye towards well 95a (the positive electrode). EOF is known to be suppressed since the dye does not move away from the positive electrode (EOF arising from a negatively-charged wall causes a bulk flow away from the positive electrode).

The polarity was then switched; an electric field equal in magnitude but opposite in direction was applied across wells at the end of the vertical channels. The dye switched direction so that it was again moving towards the positive electrode.

II The purpose of this experiment was to show that positively charge dye also could be forced to turn a corner by the application of an electric field.

Wells 95b, 95a, and 96b were filled with 40 μL of buffer solution while watching the cross intersection on a monitor. After the channels were wetted, well 96a was filled with 40 μL of buffer+dye solution. A pressure of 0.88 psi was applied to well 96a, while simultaneously applying 1.09 psi to well 96b. An electric field of 455 V/cm was applied from well 95a to well 95b.

The electric field forces the positively-charged dye towards well 95b (the negative electrode). The polarity was then switched to confirm that the dye would change direction towards well 95a.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An analytical method for separating an intact charge-switch nucleotide phosphate (NP Probe) from a phosphate detectable moiety, said method comprising:
   a) providing a sample comprising an intact NP probe with a detectable moiety attached thereto, whereupon enzymatic cleavage of said intact NP probe, which produces a phosphate detectable moiety, said phosphate detectable moiety carries a molecular charge which is different than the molecular charge of said intact NP probe; and
   b) applying an electric field to said sample, thereby separating said phosphate detectable moiety from said intact NP probe.

2. The method according to claim 1, wherein said NP probe with a detectable moiety is a labeled nucleotide triphosphate (NTP).

3. The method according to claim 2, wherein said labeled nucleotide triphosphate (NTP) having a detectable moiety is a NTP having a γ-phosphate with a detectable moiety attached thereto.

4. The method according to claim 2, wherein said charged detectable moiety when released comprises a pyrophosphate with a fluorophore moiety attached thereto.

5. The method according to claim 3, wherein said labeled NTP is incorporated into said nucleic acid primer hybridized to said target nucleic acid using said polymerase, thereby releasing said γ-phosphate with said detectable moiety attached thereto.

6. The method according to claim 5, wherein said target nucleic acid comprises a self-complementary region forming said primer.

7. The method according to claim 1, wherein the charge of said detectable moiety after release is different than said labeled nucleotide phosphate (NP) having a detectable moiety attached thereto.

8. The method according to claim 7, wherein the charge of said detectable moiety is more positive than the unincorporated labeled NP.

9. The method according to claim 7, wherein the charge of said detectable moiety attached thereto is opposite in sign compared to the unincorporated fluorescently labeled NP.

10. The method according to claim 1, further comprising
    c) measuring said detectable moiety with a measuring device.

11. The method according to claim 10, wherein said measuring device is selected from the group consisting of a charge coupled device (CCD) camera, a photodiode, a video chip, amp meter, voltage meter, and a dye-impregnated polymeric coating on optical fiber sensor.

12. The method according to claim 11, wherein said detection is via a CCD camera.

13. The method according to claim 11, wherein said detection is via a photodiode.

* * * * *